United States Patent
Briggs et al.

[11] Patent Number: 5,969,156
[45] Date of Patent: *Oct. 19, 1999

[54] CRYSTALLINE [R- (R*,R*)]-2-(4-DFLUOROPHENYL)-β,δ-DIHYDROXY-5-(1-METHYLETHYL)-3-PHENYL-4-[(PHENYLAMINO)CARBONYL]-1H-PYRROLE-1-HEPTANOIC ACID HEMI CALCIUM SALT (ATORVASTATIN)

[75] Inventors: Christopher A. Briggs; Rex A. Jennings; Robert Wade, all of Holland, Mich.; Kikuko Harasawa, Sagamihara, Japan; Shigeru Ichikawa, Machida, Japan; Kazuo Minohara; Shinsuke Nakagawa, both of Sagamihara, Japan

[73] Assignee: Warner-Lambert Company, Morris Plains, N.J.

[*] Notice: This patent is subject to a terminal disclaimer.

[21] Appl. No.: 08/945,812
[22] PCT Filed: Jul. 8, 1996
[86] PCT No.: PCT/US96/11368
   § 371 Date: Oct. 2, 1997
   § 102(e) Date: Oct. 2, 1997
[87] PCT Pub. No.: WO97/03959
   PCT Pub. Date: Feb. 6, 1997

Related U.S. Application Data
[60] Provisional application No. 60/001,452, Jul. 17, 1995.

[51] Int. Cl.$^6$ .............. C07D 207/335; A01N 43/36
[52] U.S. Cl. ............. 548/537; 514/423; 514/429
[58] Field of Search ............ 548/537; 514/423, 514/429

[56] References Cited

U.S. PATENT DOCUMENTS
5,316,765  5/1994  Folkers et al. ............ 424/94.1

FOREIGN PATENT DOCUMENTS
0409281  7/1990  European Pat. Off. .
9416693  8/1995  WIPO .

OTHER PUBLICATIONS
Bocan, Thomas et al., Antiaherosclerotic activity of inhibitors of 3–hydroxy–3–methylgutaryl coenzyme A reductase, Atherosclerosis, 111, 127–142, Dec. 1994.
Tetrahedron Letters, vol. 33, No. 17, 1992, pp. 2283–2284, Baumann, et al.
Pharmaceutical Research, vol. 10, No. 10, 1993, pp. 1461–1465, Kearney, et al.

Primary Examiner—Robert W. Ramsuer
Assistant Examiner—Dominic Keating
Attorney, Agent, or Firm—Francis J. Tinney

[57] ABSTRACT

Crystalline forms of atorvastatin and hydrates thereof are useful hypolipidemic and hypocholesterolemic agents.

44 Claims, 6 Drawing Sheets

CRYSTALLINE [R- (R*,R*)]-2-(4-DFLUOROPHENYL)-β,δ-DIHYDROXY-5-(1-METHYLETHYL)-3-PHENYL-4-[(PHENYLAMINO)CARBONYL]-1H-PYRROLE-1-HEPTANOIC ACID HEMI CALCIUM SALT (ATORVASTATIN)

This application is a 371 of PCT/US96/11368 filed Jul. 8, 1996 which is a continuation of Provisional Application No. Ser. 60/001,452, filed Jul. 17, 1995.

BACKGROUND OF THE INVENTION

The present invention relates to novel crystalline forms of atorvastatin which is known by the chemical name [R-(R*, R*)]-2-(4-fluorophenyl)-β,δ-dihydroxy-5-(1-methylethyl)-3-phenyl-4-[(phenylamino)carbonyl]-1H-pyrrole-1-heptanoic acid hemi calcium salt useful as pharmaceutical agents, to methods for their production and isolation, to pharmaceutical compositions which include these compounds and a pharmaceutically acceptable carrier, and to pharmaceutical methods of treatment. The novel crystalline compounds of the present invention are useful as inhibitors of the enzyme 3-hydroxy-3-methylglutaryl-coenzyme A reductase (HMG-CoA reductase) and are thus useful hypolipidemic and hypocholesterolemic agents.

U.S. Pat. No. 4,681,893, which is herein incorporated by reference, discloses certain trans-6-[2-(3- or 4-carboxamido-substituted-pyrrol-1-yl)alkyl]-4-hydroxy-pyran-2-ones including trans (±)-5-(4-fluorophenyl)-2-(1-methylethyl)-N,4-diphenyl-1-[(2-tetrahydro-4-hydroxy-6-oxo-2H-pyran-2-yl)ethyl]-1H-pyrrole-3-carboxamide.

U.S. Pat. No. 5,273,995, which is herein incorporated by reference, discloses the enantiomer having the R form of the ring-opened acid of trans-5-(4-fluorophenyl)-2-(1-methylethyl)-N,4-diphenyl-1-[(2-tetrahydro-4-hydroxy-6-oxo-2H-pyran-2-yl)ethyl]-1H-pyrrole-3-carboxamide, i.e., [R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid.

U.S. Pat. Nos. 5,003,080; 5,097,045; 5,103,024; 5,124,482; 5,149,837; 5,155,251; 5,216,174; 5,245,047; 5,248,793; 5,280,126; 5,397,792; and 5,342,952, which are herein incorporated by reference, disclose various processes and key intermediates for preparing atorvastatin.

Atorvastatin is prepared as its calcium salt, i.e., [R-(R*, R*)]-2-(4-fluorophenyl)-β,δ-dihydroxy-5-(1-methylethyl)-3-phenyl-4-[(phenylamino)carbonyl]-1H-pyrrole-1-heptanoic acid calcium salt (2:1). The calcium salt is desirable since it enables atorvastatin to be conveniently formulated in, for example, tablets, capsules, lozenges, powders, and the like for oral administration. Additionally, there is a need to produce atorvastatin in a pure and crystalline form to enable formulations to meet exacting pharmaceutical requirements and specifications.

Furthermore, the process by which atorvastatin is produced needs to be one which is amenable to large-scale production. Additionally, it is desirable that the product should be in a form that is readily filterable and easily dried. Finally, it is economically desirable that the product be stable for extended periods of time without the need for specialized storage conditions.

The processes in the above United States Patents disclose amorphous atorvastatin which has unsuitable filtration and drying characteristics for large-scale production and must be protected from heat, light, oxygen, and moisture.

We have now surprisingly and unexpectedly found that atorvastatin can be prepared in crystalline form. Thus, the present invention provides atorvastatin in new crystalline forms designated Form I, Form II, and Form IV. Form I atorvastatin consists of smaller particles and a more uniform size distribution than the previous amorphous product and exhibits more favorable filtration and drying characteristics. Additionally, Form I atorvastatin is purer and more stable than the amorphous product.

SUMMARY OF THE INVENTION

Accordingly, the present invention is directed to crystalline Form I atorvastatin and hydrates thereof characterized by the following X-ray powder diffraction pattern expressed in terms of the 2θ, d-spacings, and relative intensities with a relative intensity of >20% measured after 2 minutes of grinding and measured on a Siemens D-500 diffractometer with CuK$_\alpha$ radiation:

| 2θ | d | Relative Intensity (>20%) Ground 2 Minutes |
|---|---|---|
| 9.150 | 9.6565 | 42.60 |
| 9.470 | 9.3311 | 41.94 |
| 10.266 | 8.6098 | 55.67 |
| 10.560 | 8.3705 | 29.33 |
| 11.853 | 7.4601 | 41.74 |
| 12.195 | 7.2518 | 24.62 |
| 17.075 | 5.1887 | 60.12 |
| 19.485 | 4.5520 | 73.59 |
| 21.626 | 4.1059 | 100.00 |
| 21.960 | 4.0442 | 49.44 |
| 22.748 | 3.9059 | 45.85 |
| 23.335 | 3.8088 | 44.72 |
| 23.734 | 3.7457 | 63.04 |
| 24.438 | 3.6394 | 21.10 |
| 28.915 | 3.0853 | 23.42 |
| 29.234 | 3.0524 | 23.36 |

Further, the present invention is directed to crystalline Form I atorvastatin and hydrates thereof characterized by the following solid-state $^{13}$C nuclear magnetic resonance spectrum wherein chemical shift is expressed in parts per million measured on a Bruker AX-250 spectrometer:

| Assignment (7 kHz) | Chemical Shift |
|---|---|
| C12 or C25 | 182.8 |
| C12 or C25 | 178.4 |
| C16 | 166.7 (broad) and 159.3 |
| Aromatic Carbons | |
| C2–C5, C13–C18, C19–C24, C27–C32 | 137.0 |
| | 134.9 |
| | 131.1 |
| | 129.5 |
| | 127.6 |
| | 123.5 |
| | 120.9 |
| | 118.2 |
| | 113.8 |
| C8, C10 | 73.1 |
| | 70.5 |
| | 68.1 |
| | 64.9 |
| Methylene Carbons | |
| C6, C7, C9, C11 | 47.4 |
| | 41.9 |
| | 40.2 |

| Assignment (7 kHz) | Chemical Shift |
|---|---|
| C33 | 26.4 |
|  | 25.2 |
| C34 | 21.3 |

In a preferred embodiment of the first aspect of the invention, crystalline Form I atorvastatin is a trihydrate.

In a second aspect, the present invention is directed to crystalline Form II atorvastatin and hydrates thereof characterized by the following X-ray powder diffraction pattern expressed in terms of the 2θ, d-spacings, and relative intensities with a relative intensity of >20% measured after 2 minutes of grinding and measured on a Siemens D-500 diffractometer with $CuK_\alpha$ radiation:

| 2θ | d | Relative Intensity (>20%) Ground 2 Minutes |
|---|---|---|
| 5.582 | 15.8180 | 42.00 |
| 7.384 | 11.9620 | 38.63 |
| 8.533 | 10.3534 | 100.00 |
| 9.040 | 9.7741 | 92.06 |
| 12.440 (broad) | 7.1094 | 30.69 |
| 15.771 (broad) | 5.6146 | 38.78 |
| 17.120–17.360 (broad) | 5.1750–5.1040 | 63.66–55.11 |
| 19.490 | 4.5507 | 56.64 |
| 20.502 | 4.3283 | 67.20 |
| 22.706–23.159 (broad) | 3.9129–3.8375 | 49.20–48.00 |
| 25.697 (broad) | 3.4639 | 38.93 |
| 29.504 | 3.0250 | 37.86 |

Further, the second aspect of the present invention is directed to crystalline Form II atorvastatin and hydrates thereof characterized by the following solid-state $^{13}C$ nuclear magnetic resonance spectrum wherein chemical shift is expressed in parts per million measured on a Bruker AX-250 spectrometer:

| Assignment | Chemical Shift |
|---|---|
| Spinning Side Band | 209.1 |
| Spinning Side Band | 206.8 |
| C12 or C25 | 181 (broad) |
| C12 or C25 | 163 (broad) |
| C16 | 161 (broad) |
| Aromatic Carbons |  |
| C2–C5, C13–C18, C19–C24, C27–C32 | 140.5 |
|  | 134.8 |
|  | 133.3 |
|  | 129.0 |
|  | 122.9 |
|  | 121.4 |
|  | 120.3 |
|  | 119.0 |
|  | 117.1 |
|  | 115.7 |
|  | 114.7 |
| C8, C10 | 70.6 |
|  | 69.0 |
|  | 68.0 |
|  | 67.3 |
| Spinning Side Band | 49.4 |
| Spinning Side Band | 48.9 |

| Assignment | Chemical Shift |
|---|---|
| Methylene Carbons |  |
| C6, C7, C9, C11 | 43.4 |
|  | 42.3 |
|  | 41.7 |
|  | 40.2 |
| C33 | 27.5 |
| C34 | 22.8 (broad) |

In a third aspect, the present invention is directed to crystalline Form IV atorvastatin and hydrates thereof characterized by the following X-ray powder diffraction pattern expressed in terms of the 2θ, d-spacings, and relative intensities with a relative intensity of >15% measured on a Siemens D-500 diffractometer with $CuK_\alpha$ radiation:

| 2θ | d | Relative Intensity (>15%) |
|---|---|---|
| 4.889 | 18.605 | 38.45 |
| 5.424 | 16.2804 | 20.12 |
| 5.940 | 14.8660 | 17.29 |
| 7.997 | 11.0465 | 100.00 |
| 9.680 | 9.1295 | 67.31 |
| 10.416 | 8.4859 | 20.00 |
| 12.355 | 7.1584 | 19.15 |
| 17.662 | 5.0175 | 18.57 |
| 18.367 | 4.8265 | 23.50 |
| 19.200 | 4.6189 | 18.14 |
| 19.569 | 4.5327 | 54.79 |
| 21.723 | 4.0879 | 17.99 |
| 23.021 | 3.8602 | 28.89 |
| 23.651 | 3.7587 | 33.39 |
| 24.143 | 3.6832 | 17.23 |

Further, the fourth aspect of the present invention is directed to Form IV atorvastatin and hydrates thereof characterized by the following solid-state $^{13}C$ nuclear magnetic resonance spectrum wherein chemical shift is expressed as parts per million measured on a Bruker AX-250 spectrometer:

| Assignment | Chemical Shift |
|---|---|
| C12 or C25 | 186.4 |
|  | 184.9 |
| C12 or C25 | 181.4 |
|  | 179.3 |
| C16 | 166.1 (broad) |
|  | and |
|  | 159.0 (broad) |
| Aromatic Carbons |  |
| C2–C5, C13–C18, C19–C24, C27–C32 | 138.1 (broad) |
|  | 134.7 |
|  | 129.2 |
|  | 127.1 |
|  | 122.7 |
|  | 119.8 |
|  | 115.7 |
| C8, C10 | 71.5 |
|  | 67.9 |
|  | 66.3 |
|  | 63.5 |
| Methylene Carbons |  |
| C6, C7, C9, C11 | 46.1 |
|  | 43.4 |
|  | 42.1 |

-continued

| Assignment | Chemical Shift |
|---|---|
|  | 40.0 |
| C33 | 25.9 |
| C34 | 20.3 |
|  | 19.4 |
|  | 17.9 |

As inhibitors of HMG-CoA, the novel crystalline forms of atorvastatin are useful hypolipidemic and hypocholesterolemic agents.

A still further embodiment of the present invention is a pharmaceutical composition for administering an effective amount of crystalline Form I, Form II, or Form IV atorvastatin in unit dosage form in the treatment methods mentioned above. Finally, the present invention is directed to methods for production of Form I, Form II, or Form IV atorvastatin.

BRIEF DESCRIPTION OF THE DRAWINGS

The invention is further described by the following non-limiting examples which refer to the accompanying FIGS. 1 to 6, short particulars of which are given below.

Figure 1:
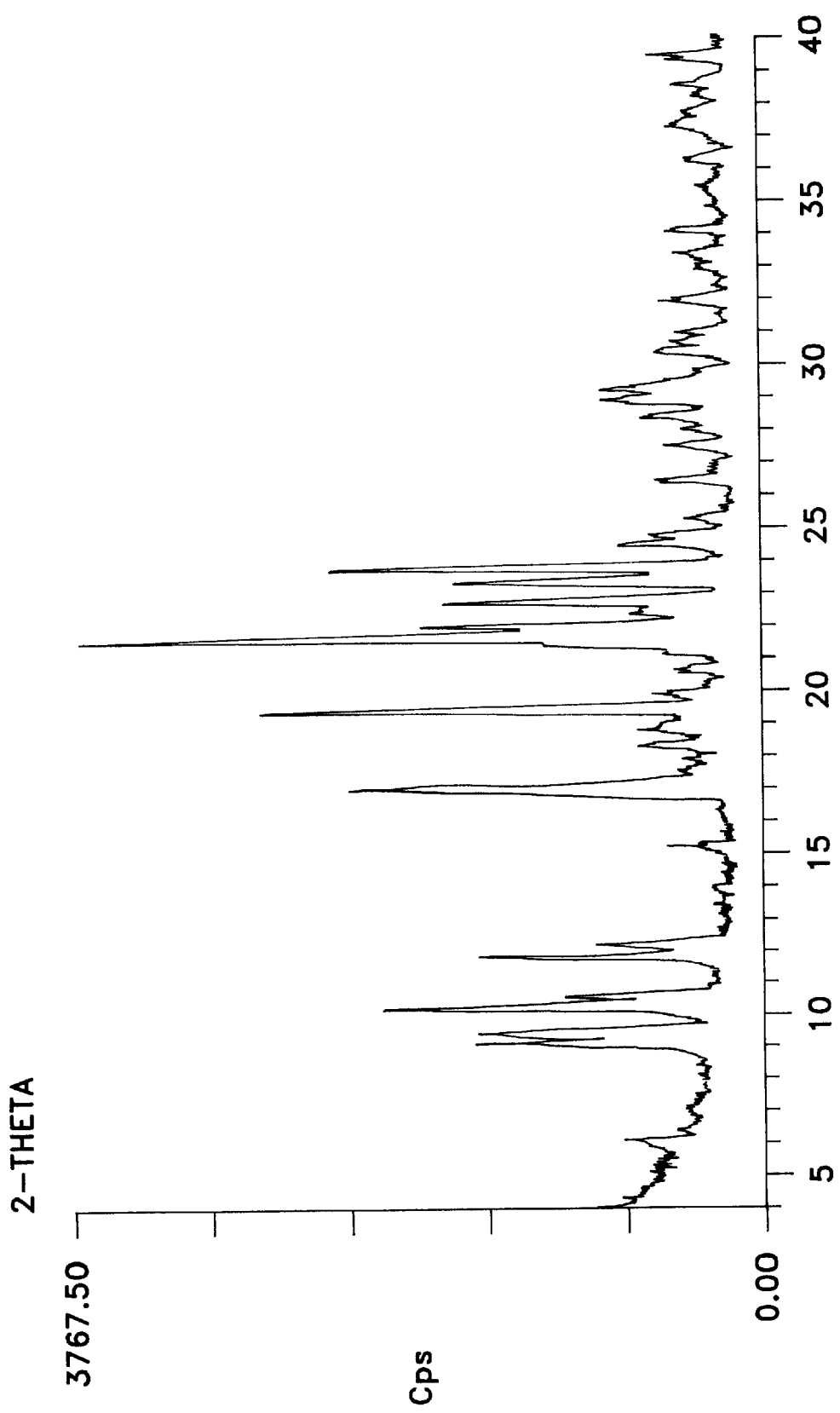
FIG. 1
Figure 2:
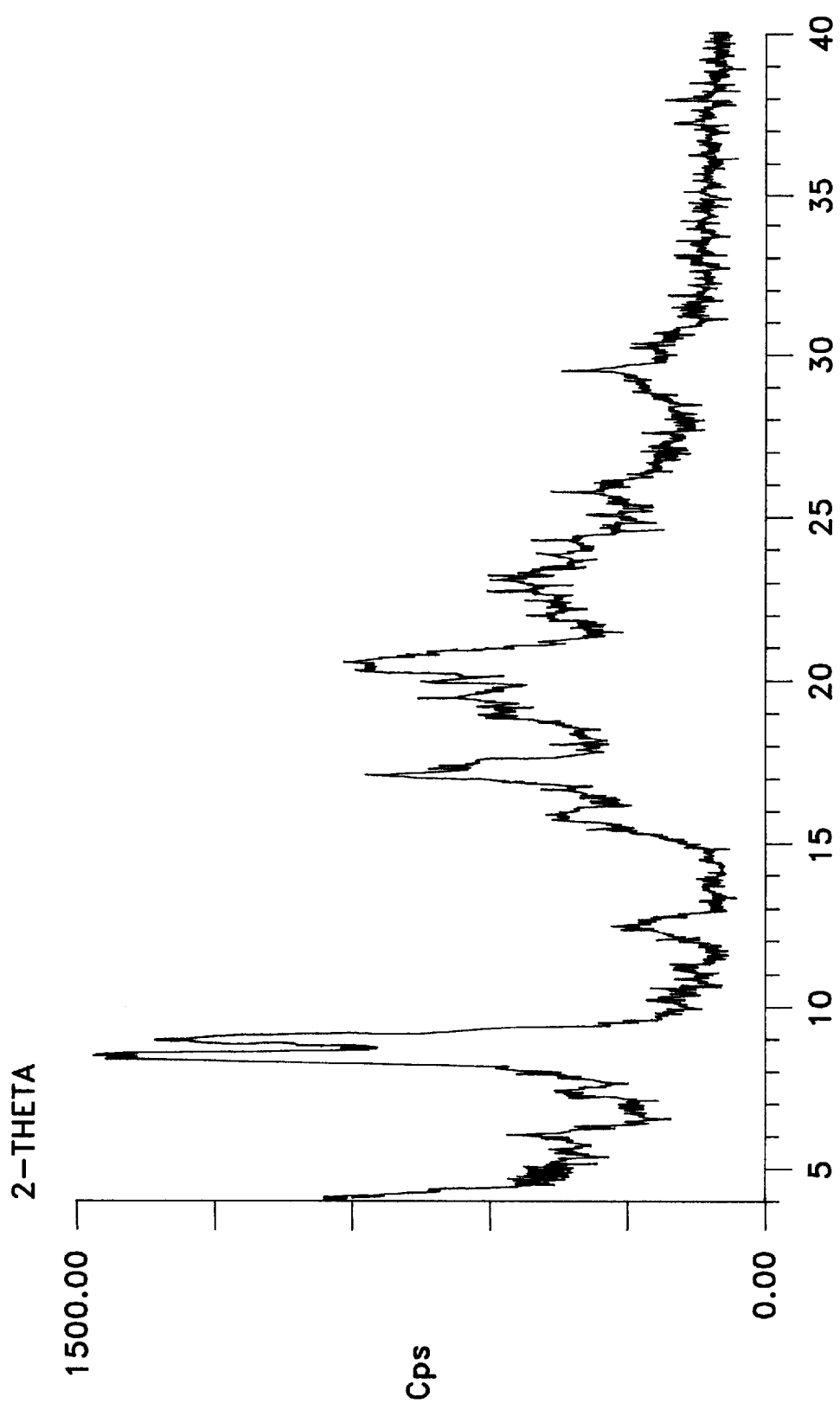
Figure 3:
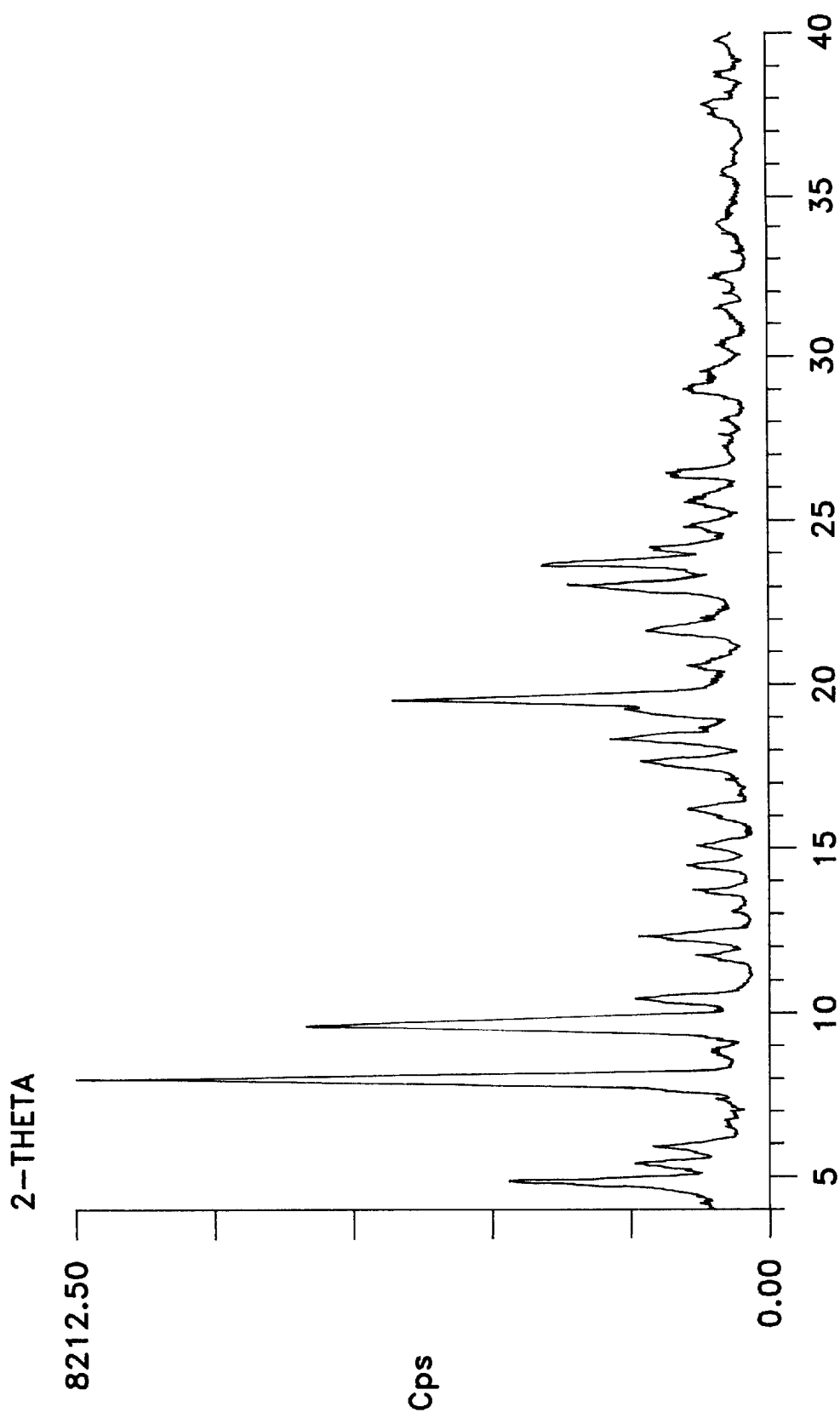
Figure 4:
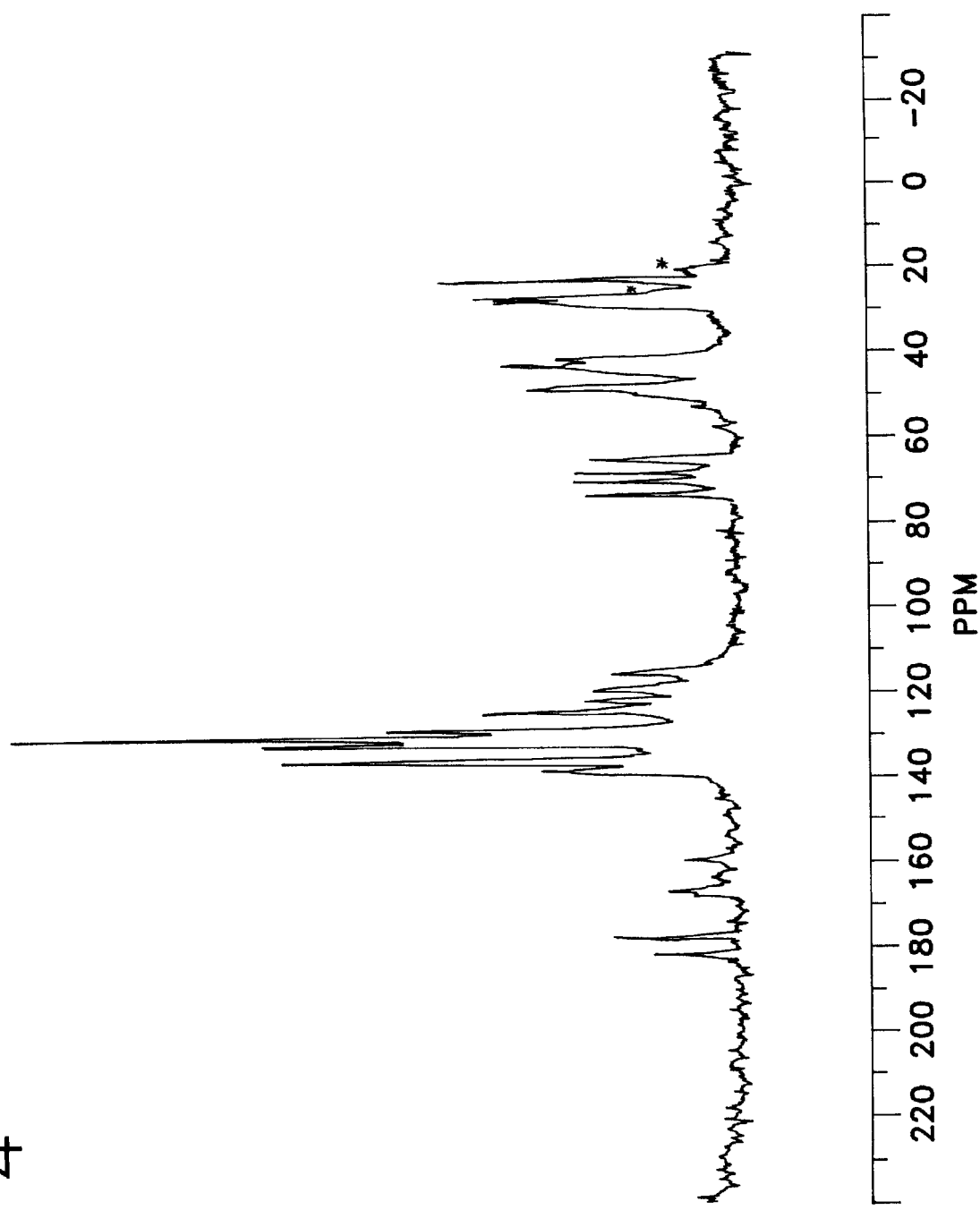
Figure 5:
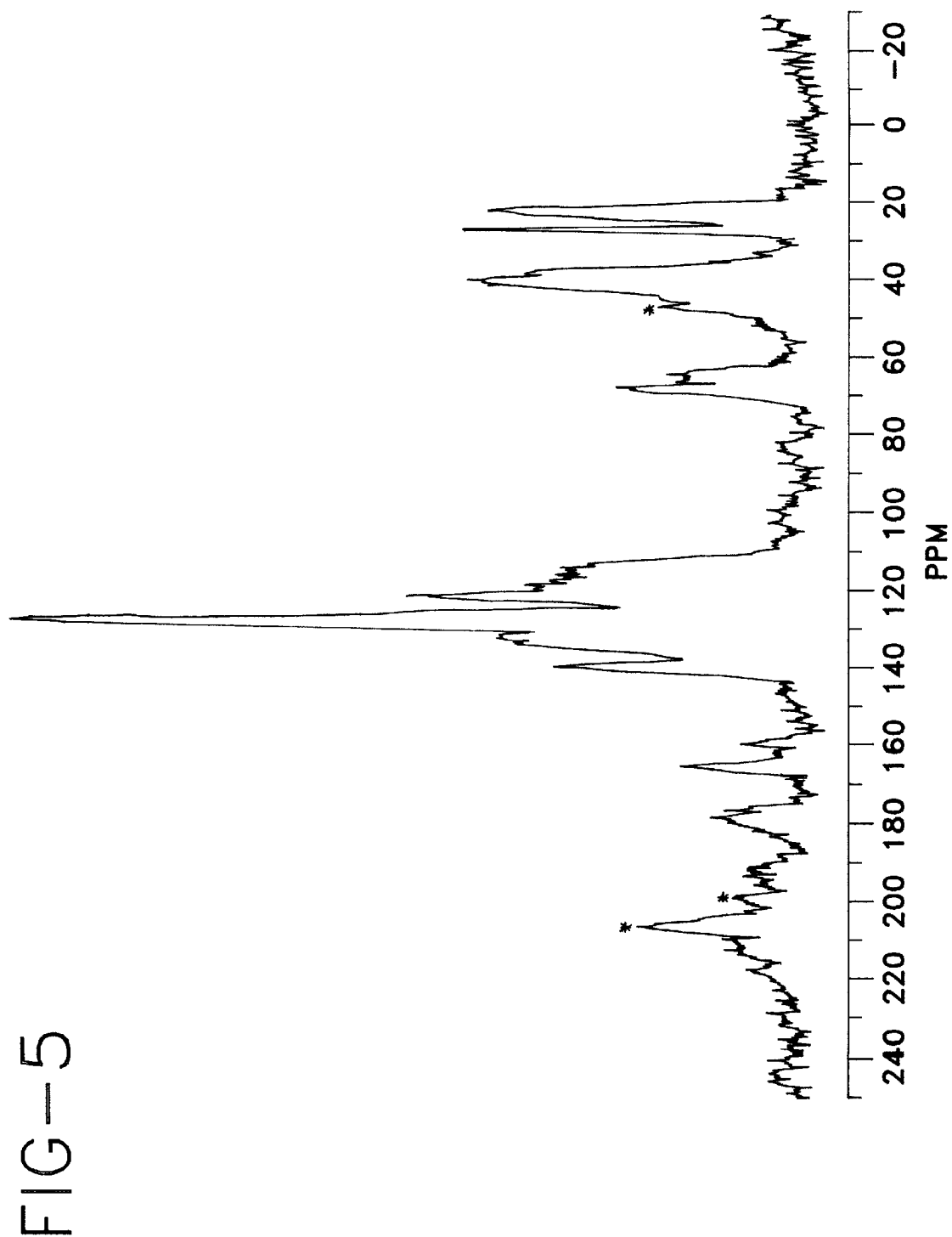
Figure 6:
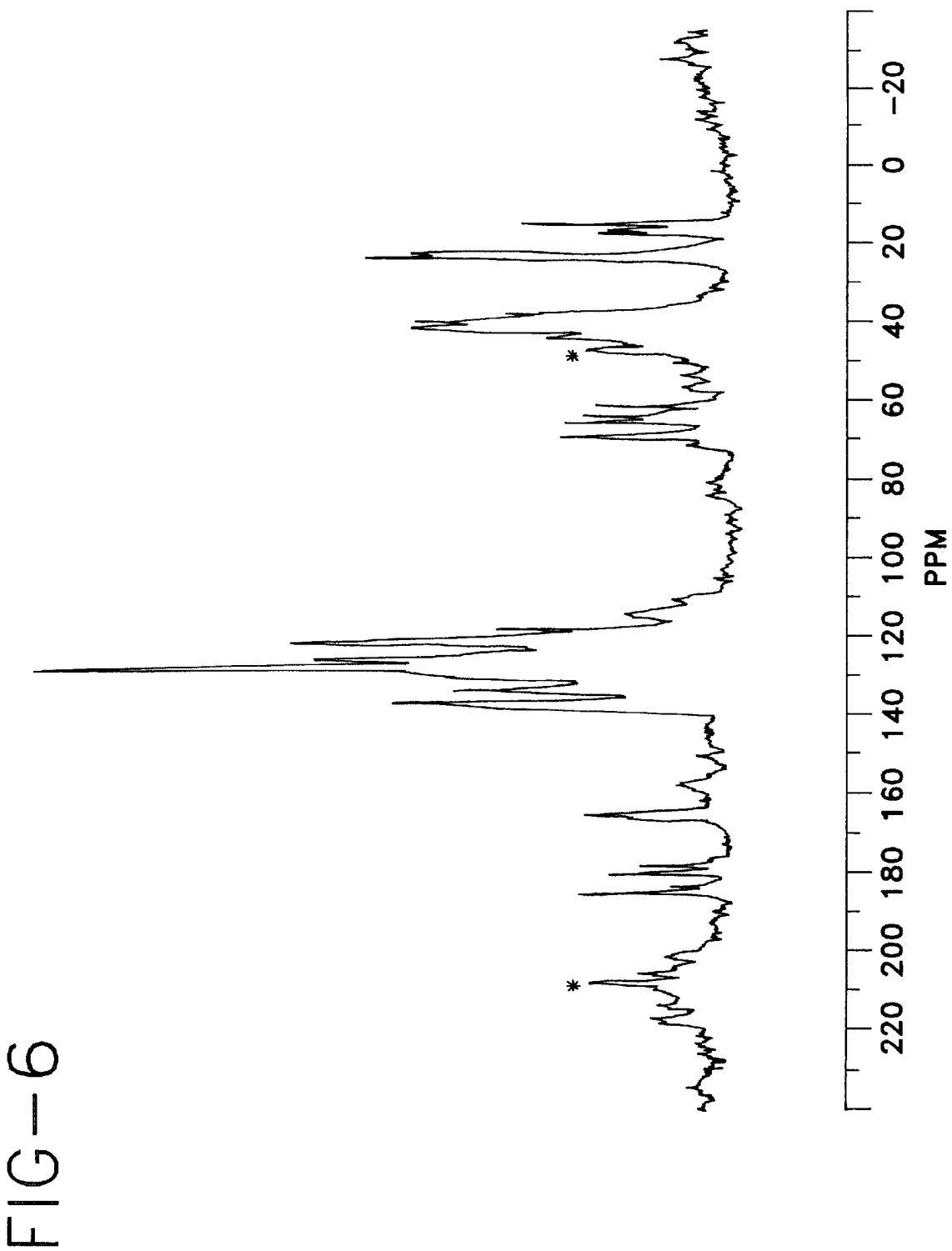

Diffractogram of Form I atorvastatin ground for 2 minutes (Y-axis=0 to maximum intensity of 3767.50 counts per second (cps))

FIG. 2

Diffractogram of Form II atorvastatin ground for 2 minutes (Y-axis=0 to maximum intensity of 1500 cps)

FIG. 3

Diffractogram of Form IV atorvastatin (Y-axis=0 to maximum intensity of 8212.5 cps).

FIG. 4

Solid-state $^{13}$C nuclear magnetic resonance spectrum with spinning side bands identified by an asterisk of Form I atorvastatin.

FIG. 5

Solid-state $^{13}$C nuclear magnetic resonance spectrum with spinning side bands identified by an asterisk of Form II atorvastatin.

FIG. 6

Solid-state $^{13}$C nuclear magnetic resonance spectrum with spinning side bands identified by an asterisk of Form IV atorvastatin.

DETAILED DESCRIPTION OF THE INVENTION

Crystalline Form I, Form II, or Form IV atorvastatin may be characterized by their X-ray powder diffraction patterns and/or by their solid state nuclear magnetic resonance spectra (NMR).

X-RAY POWDER DIFFRACTION

Forms I, II, and IV Atorvastatin

Forms I, II, or Form IV atorvastatin were characterized by their X-ray powder diffraction pattern. Thus, the X-ray diffraction patterns of Forms I, II, and Form IV atorvastatin were measured on a Siemens D-500 diffractometer with CuK$_\alpha$ radiation.

Equipment

Siemens D-500 Diffractometer-Kristalloflex with an IBM-compatible interface, software=DIFFRAC AT (SOCABIM 1986, 1992). CuK$_\alpha$ radiation (20 mA, 40 kV, λ=1.5406 Å) Slits I and II at 1°) electronically filtered by the Kevex Psi Peltier Cooled Silicon [Si(Li)]Detector (Slits: III at 1° and IV at 0.15°).

Methodology

The silicon standard is run each day to check the X-ray tube alignment.

Continuous θ/2θ coupled scan: 4.00° to 40.00° in 2θ, scan rate of 6°/min: 0.4 sec/0.04° step.

Sample tapped out of vial and pressed onto zero-background quartz in aluminum holder. Sample width 13–15 mm.

Samples are stored and run at room temperature.

Grinding/Sieving

Grinding is used to minimize intensity variations for the diffractogram disclosed herein. However, if grinding significantly altered the diffractogram or increased the amorphous content of the sample, then the diffractogram of the unground sample was used. Grinding was done in a small agate mortar and pestle. The mortar was held during the grinding and light pressure was applied to the pestle.

Ground Form II atorvastatin was sieved through a 230 mesh screen before analysis by x-ray diffraction.

Table 1 lists the 2θ, d-spacings, and relative intensities of all lines in the unground sample with a relative intensity of >20% for crystalline Form I atorvastatin. Table 1 also lists the relative intensities of the same lines in a diffractogram measured after 2 minutes of grinding. The intensities of the sample ground for 2 minutes are more representative of the diffraction pattern without preferred orientation. It should also be noted that the computer-generated, unrounded numbers are listed in this table.

TABLE 1

Intensities and Peak Locations of all Diffraction Lines With Relative Intensity Greater Than 20% for Form I Atorvastatin

| 2θ | d | Relative Intensity (>20%) No Grinding | Relative Intensity (>20%)* Ground 2 Minutes |
|---|---|---|---|
| 9.150 | 9.6565 | 37.42 | 42.60 |
| 9.470 | 9.3311 | 46.81 | 41.94 |
| 10.266 | 8.6098 | 75.61 | 55.67 |
| 10.560 | 8.3705 | 24.03 | 29.33 |
| 11.853 | 7.4601 | 55.16 | 41.74 |
| 12.195 | 7.2518 | 20.03 | 24.62 |
| 17.075 | 5.1887 | 25.95 | 60.12 |
| 19.485 | 4.5520 | 89.93 | 73.59 |
| 21.626 | 4.1059 | 100.00 | 100.00 |
| 21.960 | 4.0442 | 58.64 | 49.44 |
| 22.748 | 3.9059 | 36.95 | 45.85 |
| 23.335 | 3.8088 | 31.76 | 44.72 |
| 23.734 | 3.7457 | 87.55 | 63.04 |
| 24.438 | 3.6394 | 23.14 | 21.10 |
| 28.915 | 3.0853 | 21.59 | 23.42 |
| 29.234 | 3.0524 | 20.45 | 23.36 |

*The second relative intensity column gives the relative intensities of the diffraction lines on the original diffractogram after 2 minutes of grinding.

Table 2 lists the 2θ, d-spacings, and relative intensities of all lines in the ground/sieved sample with a relative intensity of >20% for crystalline Form II atorvastatin. It should also be noted that the computer-generated unrounded numbers are listed in this table.

TABLE 2

Intensities and Peak Locations of All
Diffraction Lines With Relative Intensity
Greater Than 20% for Form II Atorvastatin

| 2θ | d | Relative Intensity (>20%) |
|---|---|---|
| 5.582 | 15.8180 | 42.00 |
| 7.384 | 11.9620 | 38.63 |
| 8.533 | 10.3534 | 100.00 |
| 9.040 | 9.7741 | 92.06 |
| 12.440 (broad) | 7.1094 | 30.69 |
| 15.771 (broad) | 5.6146 | 38.78 |
| 17.120–17.360 (broad) | 5.1750–5.1040 | 63.66–55.11 |
| 19.490 | 4.5507 | 56.64 |
| 20.502 | 4.3283 | 67.20 |
| 22.706–23.159 (broad) | 3.9129–3.8375 | 49.20–48.00 |
| 25.697 (broad) | 3.4639 | 38.93 |
| 29.504 | 3.0250 | 37.86 |

Table 3 lists the 2θ, d-spacings, and relative intensities of all lines in the unground sample with a relative intensity of >15% for crystalline Form IV atorvastatin. It should also be noted that the computer-generated unrounded numbers are listed in this table.

TABLE 3

Intensities and Peak Locations of All
Diffraction Lines With Relative Intensity
Greater Than 15% for Form IV Atorvastatin

| 2θ | d | Relative Intensity (>15%) |
|---|---|---|
| 4.889 | 18.605 | 38.45 |
| 5.424 | 16.2804 | 20.12 |
| 5.940 | 14.8660 | 17.29 |
| 7.997 | 11.0465 | 100.00 |
| 9.680 | 9.1295 | 67.31 |
| 10.416 | 8.4859 | 20.00 |
| 12.355 | 7.1584 | 19.15 |
| 17.662 | 5.0175 | 18.57 |
| 18.367 | 4.8265 | 23.50 |
| 19.200 | 4.6189 | 18.14 |
| 19.569 | 4.5327 | 54.79 |
| 21.723 | 4.0879 | 17.99 |
| 23.021 | 3.8602 | 28.89 |
| 23.651 | 3.7587 | 33.39 |
| 24.143 | 3.6832 | 17.23 |

SOLID STATE NUCLEAR MAGNETIC RESONANCE (NMR)

Methodology

All solid-state $^{13}$C NMR measurements were made with a Bruker AX-250, 250 MHz NMR spectrometer. High resolution spectra were obtained using high-power proton decoupling and cross-polarization (CP) with magic-angle spinning (MAS) at approximately 5 kHz. The magic-angle was adjusted using the Br signal of KBr by detecting the side bands as described by Frye and Maciel (Frye J. S. and Maciel G. E., *J. Mag. Res.*, 1982;48:125). Approximately 300 to 450 mg of sample packed into a canister-design rotor was used for each experiment. Chemical shifts were referenced to external tetrakis (trimethylsilyl)silane (methyl signal at 3.50 ppm) (Muntean J. V. and Stock L. M., *J. Mag. Res.*, 1988;76:54).

Table 4 shows the solid-state NMR spectrum for crystalline Form I atorvastatin.

TABLE 4

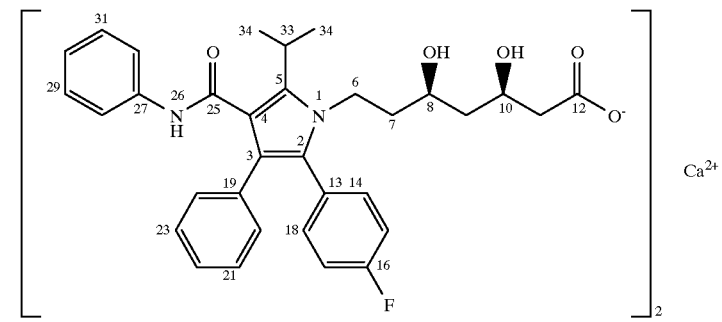

Carbon Atom Assignment and Chemical Shift for Form I Atorvastatin

| Assignment (7 kHz) | Chemical Shift |
|---|---|
| C12 or C25 | 182.8 |
| C12 or C25 | 178.4 |
| C16 | 166.7 (broad) and 159.3 |
| Aromatic Carbons C2–C5, C13–C18, C19–C24, C27–C32 | 137.0 |
| | 134.9 |
| | 131.1 |

TABLE 4-continued

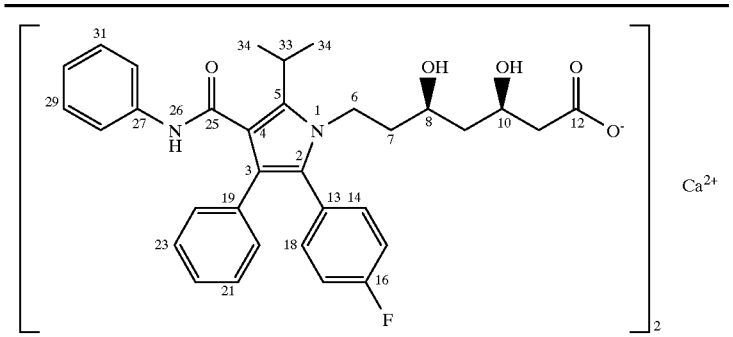

Carbon Atom Assignment and Chemical
Shift for Form I Atorvastatin

| Assignment (7 kHz) | Chemical Shift |
|---|---|
|  | 129.5 |
|  | 127.6 |
|  | 123.5 |
|  | 120.9 |
|  | 118.2 |
|  | 113.8 |
| C8, C10 | 73.1 |
|  | 70.5 |
|  | 68.1 |
|  | 64.9 |
| Methylene Carbons | 47.4 |
| C6, C7, C9, C11 | 41.9 |
|  | 40.2 |
| C33 | 26.4 |
|  | 25.2 |
| C34 | 21.3 |

Table 5 shows the solid-state NMR spectrum for crystalline Form II atorvastatin.

TABLE 5

Carbon Atom Assignment and Chemical
Shift for Form II Atorvastatin

| Assigmnent | Chemical Shift |
|---|---|
| Spinning Side Band | 209.1 |
| Spinning Side Band | 206.8 |
| C12 or C25 | 181 (broad) |
| C12 or C25 | 163 (broad) |
| C16 | 161 (broad) |
| Aromatic Carbons |  |
| C2–C5, C13–C18, C19–C24, C27–C32 | 140.5 |
|  | 134.8 |
|  | 133.3 |
|  | 129.0 |
|  | 122.9 |
|  | 121.4 |
|  | 120.3 |
|  | 119.0 |
|  | 117.1 |
|  | 115.7 |
|  | 114.7 |
|  | 70.6 |
|  | 69.0 |
| C8, C10 | 68.0 |
|  | 67.3 |
| Spinning Side Band | 49.4 |
| Spinning Side Band | 48.9 |

TABLE 5-continued

Carbon Atom Assignment and Chemical
Shift for Form II Atorvastatin

| Assignment | Chemical Shift |
|---|---|
| Methylene Carbons |  |
| C6, C7, C9, C11 | 43.4 |
|  | 42.3 |
|  | 41.7 |
|  | 40.2 |
| C33 | 27.5 |
| C34 | 22.8 (broad) |

Table 6 shows the solid-state NMR spectrum for crystalline Form IV atorvastatin.

TABLE 6

Carbon Atom Assignment and Chemical Shift
for Form IV Atorvastatin

| Assignment | Chemical Shift |
|---|---|
| C12 or C25 | 186.4 |
|  | 184.9 |
| C12 or C25 | 181.4 |
|  | 179.3 |
| C16 | 166.1 (broad) and 159.0 (broad) |

TABLE 6-continued

Carbon Atom Assignment and Chemical Shift
for Form IV Atorvastatin

| Assignment | Chemical Shift |
|---|---|
| Aromatic Carbons | |
| C2–C5, C13–C18, C19–C24, C27–C32 | 138.1 (broad) |
| | 134.7 |
| | 129.2 |
| | 127.1 |
| | 122.7 |
| | 119.8 |
| | 115.7 |
| C8, C10 | 71.5 |
| | 67.9 |
| | 66.3 |
| | 63.5 |
| Methylene Carbons | |
| C6, C7, C9, C11 | 46.1 |
| | 43.4 |
| | 42.1 |
| | 40.0 |
| C33 | 25.9 |
| C34 | 20.3 |
| | 19.4 |
| | 17.9 |

Crystalline Form I, Form II, and Form IV atorvastatin of the present invention may exist in anhydrous forms as well as hydrated forms. In general, the hydrated forms, are equivalent to unhydrated forms and are intended to be encompassed within the scope of the present invention. Crystalline Form I atorvastatin contains about 1 to 8 mol of water. Preferably, Form I atorvastatin contains 3 mol of water.

The present invention provides a process for the preparation of crystalline Form I atorvastatin which comprises crystallizing atorvastatin from a solution in solvents under conditions which yield crystalline Form I atorvastatin.

The precise conditions under which crystalline Form I atorvastatin is formed may be empirically determined and it is only possible to give a number of methods which have been found to be suitable in practice.

Thus, for example, crystalline Form I atorvastatin may be prepared by crystallization under controlled conditions. In particular, it can be prepared either from an aqueous solution of the corresponding basic salt such as, an alkali metal salt, for example, lithium, potassium, sodium, and the like; ammonia or an amine salt; preferably, the sodium salt by addition of a calcium salt, such as, for example, calcium acetate and the like, or by suspending amorphous atorvastatin in water. In general, the use of a hydroxylic co-solvent such as, for example, a lower alkanol, for example methanol and the like, is preferred.

When the starting material for the preparation of the desired crystalline Form I atorvastatin is a solution of the corresponding sodium salt, one preferred preparation involves treating a solution of the sodium salt in water containing not less than about 5% v/v methanol, preferably about 5% to 33% v/v methanol, particularly preferred about 10% to 15% v/v methanol, with an aqueous solution of calcium acetate, preferably at an elevated temperature at up to about 70° C. such as, for example, about 45–60° C., particularly preferred about 47–52° C. It is preferable to use calcium acetate and, in general, 1 mole of calcium acetate to 2 moles of the sodium salt of atorvastatin. Under these conditions, calcium salt formation as well as crystallization should preferably be carried out at an elevated temperature, for example within the above-mentioned temperature ranges. It has been found that it may be advantageous to include in the starting solution a small amount of methyl tert-butyl ether (MTBE) such as, for example, about 7% w/w. It has frequently been found desirable to add "seeds" of crystalline Form I atorvastatin to the crystallization solution in order to consistently produce crystalline Form I atorvastatin.

When the starting material is amorphous atorvastatin or a combination of amorphous and crystalline Form I Atorvastatin, the desired crystalline Form I atorvastatin may be obtained by suspending the solid in water containing up to about 40% v/v, such as, for example, about 0% to 20% v/v, particularly preferred about 5% to 15% v/v co-solvent such as, for example, methanol, ethanol, 2-propanol, acetone, and the like until conversion to the required form is complete, followed by filtration. It has frequently been found desirable to add "seeds" of crystalline Form I atorvastatin to the suspension in order to ensure complete conversion to crystalline Form I atorvastatin. Alternatively, a water-wet cake consisting principally of amorphous atorvastatin can be heated at elevated temperatures such as, for example, up to about 75° C., particularly preferred about 65–70° C., until a significant amount of crystalline Form I atorvastatin is present, whereupon the amorphous/crystalline Form I mixture can be slurried as described above.

Crystalline Form I atorvastatin is significantly easier to isolate than amorphous atorvastatin and can be filtered from the crystallization medium after cooling, and washed and dried. For example, filtration of a 50 mL slurry of crystalline Form I atorvastatin was complete within 10 seconds. A similarly sized sample of amorphous atorvastatin took more than an hour to filter.

The present invention also provides a process for the preparation of crystalline Form II atorvastatin which comprises suspending atorvastatin in solvents under conditions which yield crystalline Form II atorvastatin.

The precise conditions under which Form II of crystalline atorvastatin is formed may be empirically determined and it is only possible to give a method which has been found to be suitable in practice.

Thus, for example, when the starting material is amorphous, a combination of amorphous and Form I, or crystalline Form I atorvastatin, the desired Form II of crystalline atorvastatin may be obtained by suspending the solid in methanol containing about 40% to about 50% water until conversion to the required form is complete, followed by filtration.

The present invention also provides a process for the preparation of crystalline Form IV atorvastatin which comprises crystallizing atorvastatin from a solution thereof in solvents under conditions which yield crystalline Form IV atorvastatin.

The precise conditions under which Form IV of crystalline atorvastatin is formed may be empirically determined and it is only possible to give a method which has been found to be suitable in practice.

Thus, for example, when the starting material is Form I of crystalline atorvastatin, the desired Form IV of crystalline atorvastatin may be obtained by dissolving the solid in methanol whereupon crystalline Form IV precipitates.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either compounds or a corresponding pharmaceutically acceptable salt of a compound of the present invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from two or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, retention enemas, and emulsions, for example water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.5 mg to 100 mg, preferably 2.5 mg to 80 mg according to the particular application and the potency of the active component. The composition can, if desired, also contain other compatible therapeutic agents.

In therapeutic use as hypolipidemic and/or hypocholesterolemic agents, the crystalline Forms I, II, and Form IV atorvastatin utilized in the pharmaceutical method of this invention are administered at the initial dosage of about 2.5 mg to about 80 mg daily. A daily dose range of about 2.5 mg to about 20 mg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired.

The following nonlimiting examples illustrate the inventors' preferred methods for preparing the compounds of the invention.

EXAMPLE 1

[R-(R*,R*)]-2-(4-Fluorophenyl)-β,δ-dihydroxy-5-(1-methylethyl)-3-phenyl-4-[(phenylamino)carbonyl]-1H-pyrrole-1-heptanoic acid hemi calcium salt (Form I Atorvastatin)

Method A

A mixture of (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide (atorvastatin lactone) (U.S. Pat. No. 5,273,995) (75 kg), methyl tertiary-butyl ether (MTBE) (308 kg), methanol (190 L) is reacted with an aqueous solution of sodium hydroxide (5.72 kg in 950 L) at 48–58° C. for 40 to 60 minutes to form the ring-opened sodium salt. After cooling to 25–35° C., the organic layer is discarded, and the aqueous layer is again extracted with MTBE (230 kg). The organic layer is discarded, and the MTBE saturated aqueous solution of the sodium salt is heated to 47–52° C. To this solution is added a solution of calcium acetate hemihydrate (11.94 kg) dissolved in water (410 L), over at least 30 minutes. The mixture is seeded with a slurry of crystalline Form I atorvastatin (1.1 kg in 11 L water and 5 L methanol) shortly after addition of the calcium acetate solution. The mixture is then heated to 51–57° C. for at least 10 minutes and then cooled to 15–40° C. The mixture is filtered, washed with a solution of water (300 L) and methanol (150 L) followed by water (450 L). The solid is dried at 60–70° C. under vacuum for 3 to 4 days to give crystalline Form I atorvastatin (72.2 kg).

Method B

Amorphous atorvastatin (9 g) and crystalline Form I atorvastatin (1 g) are stirred at about 40° C. in a mixture of water (170 mL) and methanol (30 mL) for a total of 17 hours. The mixture is filtered, rinsed with water, and dried at 70° C. under reduced pressure to give crystalline Form I atorvastatin (9.7 g).

EXAMPLE 2

[R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid hemi calcium salt
(Form II Atorvastatin)

A mixture of amorphous and crystalline Form I atorvastatin (100 g) was suspended in a mixture of methanol (1200 mL) and water (800 mL) and stirred for 3 days. The material was filtered, dried at 70° C. under reduced pressure to give crystalline Form II atorvastatin.

EXAMPLE 3

[R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid hemi calcium salt
(Form IV Atorvastatin)

A mixture of (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide (atorvastatin lactone) (U.S. Pat. No. 5,273,995) (12 kg), MTBE (50 kg), methanol (30 L) is reacted with an aqueous solution of sodium hydroxide (1.83 kg in 150 L) at 50–55° C. for 30–45 minutes to form the ring-opened sodium salt. After cooling to 20–25° C., the organic layer is discarded and the aqueous layer is again extracted with MTBE (37 kg). The organic layer is discarded and the aqueous solution of the sodium salt is heated to 70–80° C. and the residual MTBE is removed by distillation. The solution is then cooled to 60–70° C. To this solution is added a solution of calcium acetate hemihydrate (1.91 kg) dissolved in water/methanol (72 L water+16 L methanol). The mixture is seeded with crystalline Form I atorvastatin (180 g) shortly after addition of the calcium acetate solution. The mixture is heated at 65–75° C. for at least 5 minutes and then cooled to 50–55° C. The mixture is filtered and slurried in methanol (about 200 L) at 55–65° C. and then cooled to 25–30° C. and filtered. The solid is dried at 66–70° C. under vacuum to give Form IV of crystalline atorvastatin (about 3 kg isolated).

We claim:

1. A crystalline Form I atorvastatin hydrate having an X-ray powder diffraction containing at least one of the following 2θ values measured using CuK$_\alpha$ radiation: 11.9 or 22.0.

2. A crystalline Form I atorvastatin hydrate having an X-ray powder diffraction containing the following 2θ values measured using Cuk$_\alpha$ radiation: 11.9, 21.6 and 22.0.

3. A crystalline Form I atorvastatin hydrate having an X-ray powder diffraction containing the following 2θ values measured using CuK$_\alpha$ radiation: 17.1, 19.5 and 21.6.

4. A crystalline Form I atorvastatin hydrate having an X-ray powder diffraction containing the following 2θ values measured using Cuk$_\alpha$ radiation: 9.2, 9.5, 10.3, 10.6, 11.9, 12.2, 17.1, 19.5, 21.6, 22.0, 22.7, 23.3, 23.7, 24.4, 28.9 and 29.2.

5. A crystalline Form I atorvastatin hydrate having an X-ray powder diffraction containing the following 2θ values measured using Cuk$_\alpha$ radiation: 9.150, 9.470, 10.266, 10.560, 11.853, 12.195, 17.075, 19.485, 21.626, 21.960, 22.748, 23.335, 23.734, 24.438, 28.915 and 29.234.

6. A crystalline Form I atorvastatin hydrate characterized by solid state $^{13}$C nuclear magnetic resonance having a chemical shift difference between the lowest ppm resonance and another resonance of 5.1 or 51.8.

7. A crystalline Form I atorvastatin hydrate characterized by solid state $^{13}$C nuclear magnetic resonance and having the following chemical shift differences between the lowest ppm resonance and other resonances: 3.9, 5.1, 43.6, 46.8, 49.2 and 51.8.

8. A crystalline Form I atorvastatin hydrate characterized by solid-state $^{13}$C nuclear magnetic resonance having the following chemical shift differences between the lowest ppm resonance and other resonances: 3.9, 5.1, 18.9, 20.6, 26.1, 43.6, 46.8, 49.2, 51.8, 92.5, 96.9, 99.6, 102.2, 106.3, 108.2, 109.8, 113.6, 115.7, 138.0, 145.4, 157.1 and 161.5.

9. A crystalline Form I atorvastatin hydrate characterized by solid-state $^{13}$C nuclear magnetic resonance having the following chemical shifts expressed in parts per million: 21.3. 25.2, 26.4, 40.2, 41.9, 47.4, 64.9, 68.1, 70.5, 73.1, 113.8, 118.2, 120.9, 123.5, 127.6, 129.5, 131.1, 134.9, 137.0, 159.3, 166.7 (broad), 178.4 and 182.8.

10. The crystalline Form I atorvastatin hydrate of claim 1 containing about 1 to 8 moles of water.

11. The crystalline Form I atorvastatin hydrate of claim 1 containing 3 moles of water.

12. The crystalline Form I atorvastatin hydrate of claim 2 containing about 1 to 8 moles of water.

13. The crystalline Form I atorvastatin hydrate of claim 2 containing 3 moles of water.

14. The crystalline Form I atorvastatin hydrate of claim 3 containing about 1 to 8 moles of water.

15. The crystalline Form I atorvastatin hydrate of claim 3 containing 3 moles of water.

16. The crystalline Form I atorvastatin hydrate of claim 4 containing about 1 to 8 moles of water.

17. The crystalline Form I atorvastatin hydrate of claim 4 containing 3 moles of water.

18. The crystalline Form I atorvastatin hydrate of claim 5 containing about 1 to 8 moles of water.

19. The crystalline Form I atorvastatin hydrate of claim 5 containing 3 moles of water.

20. The crystalline Form I atorvastatin hydrate of claim 6 containing about 1 to 8 moles of water.

21. The crystalline Form I atorvastatin hydrate of claim 6 containing 3 moles of water.

22. The crystalline Form I atorvastatin hydrate of claim 7 containing about 1 to 8 moles of water.

23. The crystalline Form I atorvastatin hydrate of claim 7 containing 3 moles of water.

24. The crystalline Form I atorvastatin hydrate of claim 8 containing about 1 to 8 moles of water.

25. The crystalline Form I atorvastatin hydrate of claim 8 containing 3 moles of water.

26. The crystalline Form I atorvastatin hydrate of claim 9 containing about 1 to 8 moles of water.

27. The crystalline Form I atorvastatin hydrate of claim 9 containing 3 moles of water.

28. Crystalline Form II atorvastatin or a hydrate thereof having an X-ray powder diffraction containing the following 2θ values measured using CuK$_\alpha$ radiation: 9.0 and 20.5.

29. Crystalline Form II atorvastatin or a hydrate thereof having an X-ray powder diffraction containing the following 2θ values measured using CuK$_\alpha$ radiation: 8.5 and 9.0.

30. Crystalline Form II atorvastatin or a hydrate thereof having an X-ray powder diffraction containing the following 2θ values measured using CuK$_\alpha$ radiation: 5.6, 7.4, 8.5, 9.0, 12.4 (broad), 15.8 (broad), 17.1–17.4 (broad), 19.5, 20.5, 22.7–23.2 (broad), 25.7 (broad) and 29.5.

31. Crystalline Form II atorvastatin or a hydrate thereof having an X-ray powder diffraction containing the following 2θ values measured using Cuk$_\alpha$ radiation: 5.582, 7.384, 8.533, 9.040, 12.440 (broad), 15.771 (broad), 17.120–17.360 (broad), 19.490, 20.502, 22.706–23.159 (broad), 25.697 (broad) and 29.504.

32. Crystalline Form II atorvastatin or a hydrate thereof characterized by solid state $^{13}$C nuclear magnetic resonance having a chemical shift difference between the lowest ppm resonance and another resonance of 4.7 or 47.8.

33. Crystalline Form II atorvastatin or a hydrate thereof characterized by solid state $^{13}$C nuclear magnetic resonance having the following chemical shift differences between the lowest ppm resonance and other resonances: 4.7, 44.5, 45.2, 46.2 and 47.8.

34. Crystalline Form II atorvastatin or a hydrate thereof characterized by solid-state $^{13}$C nuclear magnetic resonance having the following chemical shift differences between the lowest ppm resonance and other resonances: 4.7, 17.4, 18.9, 19.5, 20.6, 44.5, 45.2, 46.2, 47.8, 91.9, 92.9, 94.3, 96.2, 97.5, 98.6, 100.1, 106.2, 110.5, 112.0, 117.7, 138.2, 140.2 and 158.2.

35. Crystalline Form II atorvastatin or a hydrate thereof characterized by solid-state $^{13}$C nuclear magnetic resonance having the following chemical shifts expressed in parts per million: 22.8 (broad), 27.5, 40.2, 41.7, 42.3, 43.4, 67.3, 68.0, 69.0, 70.6, 114.7, 115.7, 117.1, 119.0, 120.3, 121.4, 122.9, 129.0, 133.3, 134.8, 140.5, 161 (broad), 163 (broad) and 181 (broad).

36. Crystalline Form IV atorvastatin or a hydrate thereof having an X-ray powder diffraction containing at least one of the following 2θ values measured using CuK$_\alpha$ radiation: 8.0 or 9.7.

37. Crystalline Form IV atorvastatin or a hydrate thereof having an X-ray powder diffraction containing the following 2θ values measured using CuK$_\alpha$ radiation: 4.9, 8.0 and 9.7.

38. Crystalline Form IV atorvastatin or a hydrate thereof having an X-ray powder diffraction containing the following 2θ values measured using CuK$_\alpha$ radiation: 8.0, 9.7 and 19.6.

39. Crystalline Form IV atorvastatin or a hydrate thereof having an X-ray powder diffraction containing the following 2θ values measured using CuK$_\alpha$ radiation: 4.9, 5.4, 5.9, 8.0, 9.7, 10.4, 12.4, 17.7, 18.4, 19.2, 19.6, 21.7, 23.0, 23.7 and 24.1.

40. Crystalline Form IV atorvastatin or a hydrate thereof having an X-ray powder diffraction containing the following 2θ values measured using CuK$_\alpha$ radiation: 4.889, 5.424, 5.940, 7.997, 9.680, 10.416, 12.355, 17.662, 18.367, 19.200, 19.569, 21.723, 23.021, 23.651 and 24.143.

41. Crystalline Form IV atorvastatin or a hydrate thereof characterized by solid state $^{13}$C nuclear magnetic resonance having a chemical shift difference between the lowest ppm resonance and another resonance of 8.0 or 53.6.

42. Crystalline Form IV atorvastatin or a hydrate thereof characterized by solid state $^{13}$C nuclear magnetic resonance having the following chemical shift differences between the lowest ppm resonance and other resonances: 1.5, 2.4, 8.0, 45.6, 48.4, 50.0 and 53.6.

43. Crystalline Form IV atorvastatin or a hydrate thereof characterized by solid-state $^{13}$C nuclear magnetic resonance having the following chemical shift differences between the lowest ppm resonance and other resonances: 1.5, 2.4, 8.0, 22.1, 24.2, 25.5, 28.2, 45.6, 48.4, 50.0, 53.6, 97.8, 101.9, 104.8, 109.2, 111.3, 116.8, 120.2, 141.1, 148.2, 161.4, 163.5, 167.0 and 168.5.

44. Crystalline Form IV atorvastatin or a hydrate thereof characterized by solid-state $^{13}$C nuclear magnetic resonance having the following chemical shifts expressed in parts per million: 17.9, 19.4, 20.3, 25.9, 40.0, 42.1, 43.4, 46.1, 63.5, 66.3, 67.9, 71.5, 115.7, 119.8, 122.7, 127.1, 129.2, 134.7, 138.1 (broad), 159.0 (broad), 166.1 (broad), 179.3, 181.4, 184.9 and 186.4.

* * * * *

(12) EX PARTE REEXAMINATION CERTIFICATE (5531st)
United States Patent
Briggs et al.

(10) Number: US 5,969,156 C1
(45) Certificate Issued: *Sep. 26, 2006

(54) CRYSTALLINE [R-(R*,R*)]-2-(4-FLUOROPHENYL)-β,δ-DIHYDROXY-5-(1-METHYLETHYL)-3-PHENYL-4-[(PHENYLAMINO)CARBONYL]-1H-PYRROLE-1-HEPTANOIC ACID HEMI CALCIUM SALT (ATORVASTATIN)

(75) Inventors: Christopher A. Briggs, Holland, MI (US); Rex A. Jennings, Holland, MI (US); Robert Wade, Holland, MI (US); Kikuko Harasawa, Sagamihara (JP); Shigeru Ichikawa, Machida (JP); Kazuo Minohara, Sagamihara (JP); Shinsuke Nakagawa, Sagamihara (JP)

(73) Assignee: Warner-Lambert Company, Morris Plains, NJ (US)

Reexamination Request:
No. 90/007,209, Sep. 17, 2004

Reexamination Certificate for:
Patent No.: 5,969,156
Issued: Oct. 19, 1999
Appl. No.: 08/945,812
Filed: Sep. 29, 1997

(*) Notice: This patent is subject to a terminal disclaimer.

(22) PCT Filed: Jul. 8, 1996

(86) PCT No.: PCT/US96/11368
§ 371 (c)(1),
(2), (4) Date: Oct. 2, 1997

(87) PCT Pub. No.: WO97/03959
PCT Pub. Date: Feb. 6, 1997

Related U.S. Application Data
(60) Provisional application No. 60/001,452, filed on Jul. 17, 1995.

(51) Int. Cl.
*A61K 31/40* (2006.01)
*C07D 207/00* (2006.01)
*A01N 43/36* (2006.01)

(52) U.S. Cl. .................. 548/337; 514/429; 514/423
(58) Field of Classification Search ............ 514/423; 548/537, 530
See application file for complete search history.

(56) References Cited

U.S. PATENT DOCUMENTS

| | | |
|---|---|---|
| 4,647,576 A | 3/1987 | Hoefle et al. |
| 4,681,893 A | 7/1987 | Roth |
| 5,003,080 A | 3/1991 | Butler et al. |
| 5,082,650 A | 1/1992 | Folkers et al. |
| 5,097,045 A | 3/1992 | Butler et al. |
| 5,103,024 A | 4/1992 | Millar et al. |
| 5,124,482 A | 6/1992 | Butler et al. |
| 5,149,837 A | 9/1992 | Butler et al. |
| 5,155,251 A | 10/1992 | Butler et al. |
| 5,216,174 A | 6/1993 | Butler et al. |
| 5,245,047 A | 9/1993 | Butler et al. |
| 5,248,793 A | 9/1993 | Millar et al. |
| 5,273,995 A | 12/1993 | Roth |
| 5,280,126 A | 1/1994 | Butler et al. |
| 5,298,627 A | 3/1994 | Butler et al. |
| 5,342,952 A | 8/1994 | Butler et al. |
| 5,385,929 A | 1/1995 | Bjorge et al. |
| 5,397,792 A | 3/1995 | Butler et al. |
| 5,446,054 A | 8/1995 | Butler et al. |
| 5,470,981 A | 11/1995 | Butler et al. |
| 5,489,690 A | 2/1996 | Butler et al. |
| 5,489,691 A | 2/1996 | Butler et al. |
| 5,510,488 A | 4/1996 | Butler et al. |
| 5,686,104 A | 11/1997 | Mills et al. |
| 5,798,375 A | 8/1998 | Tsujita et al. |
| 6,087,511 A | 7/2000 | Lin et al. |
| 6,121,461 A | 9/2000 | McKenzie |
| 6,126,971 A | 10/2000 | Mills et al. |
| 6,159,997 A | 12/2000 | Tsujita et al. |
| 6,274,740 B1 | 8/2001 | Lin et al. |
| 6,362,236 B1 | 3/2002 | Aviram et al. |
| 6,380,214 B1 | 4/2002 | Gant et al. |
| 6,455,574 B1 | 9/2002 | Buck |
| 6,605,636 B1 * | 8/2003 | Aronhime et al. .......... 514/423 |
| 6,605,729 B1 * | 8/2003 | Byrn et al. ............... 548/537 |
| 2003/0199492 A1 | 10/2003 | Scott |

FOREIGN PATENT DOCUMENTS

| | | |
|---|---|---|
| EP | 0 247 633 | 12/1987 |
| EP | 0 330 172 | 8/1989 |
| EP | 0 553 213 | 8/1993 |
| EP | 0 680 320 | 11/1995 |
| EP | 0 680 963 | 11/1995 |
| EP | 0 687 263 | 12/1995 |
| EP | 0 753 298 | 1/1997 |
| EP | 0 839 132 | 5/1998 |
| EP | 0 848 704 | 6/1998 |
| EP | 1 003 503 | 5/2000 |
| EP | 1 009 400 | 6/2000 |
| EP | 1 047 421 | 11/2000 |
| EP | 1 061 073 | 12/2000 |
| EP | 1 187 826 | 3/2002 |
| WO | WO-89 07598 | 8/1989 |
| WO | WO-92 06968 | 4/1992 |
| WO | WO-94 20492 | 9/1994 |
| WO | WO-97 03958 | 2/1997 |
| WO | WO-97 03960 | 2/1997 |
| WO | WO-99 11259 | 3/1999 |
| WO | WO-99 11260 | 3/1999 |
| WO | WO-99 26583 | 6/1999 |
| WO | WO-00 71532 | 11/2000 |

OTHER PUBLICATIONS

USP 23, pp. 1843–1844 (1995).

Ip et al., "High Resolution Spectroscopic Evidence and Solution Calorimetry Studies on the Polymorphs of Enalapril Maleate", International Journal of Pharmaceutics, 28, pp. 183–191 (1986).

(Continued)

Primary Examiner—Deborah C. Lambkin

(57) ABSTRACT

Crystalline forms of atorvastatin and hydrates thereof are useful hypolipidemic and hypocholesterolemic agents.

OTHER PUBLICATIONS

Mullins et al., "Some Pharmaceutical Properties of Novobiocin", J. American Pharm. Assoc., vol. 49, No. 4, pp. 245–248 (1960).

John W. Poole, "Effects of Formulation and Dosage Form on Drug Bioavailability", Principles and Perspectives in Drug Bioavailability, pp. 59–89 (1979).

The Merck Index, 12$^{th}$ Edition, Monograph No. 897 (atorvastatin) (1996).

Roth et al., "Inhibitors of Cholesterol Biosynthesis. 3. Tetrahydro–4–hydroxy–6–[2–(1H–pyrrol–1–yl) ethyl]–2H–pyran–2–one Inhibitors of HMG–CoA Reductase. 2. Effects of Introducing Substituents at Positions Three and Four of the Pyrrole Nucleus", J. of Med. Chem., 1991, vol. 34, No. 1, pp. 357–366.

Roth et al., "Inhibitors of Cholesterol Biosynthesis. 1. trans–6–(2–Pyrrol–1–ylethyl)–4–hydroxypyran–2–ones, a Novel Series of HMG–CoA Reductase Inhibitors. 1. Effects of Structural Modifications at the 2– and 5–Positions of the Pyrrole Nucleus", J. of Med. Chem., 1990, vol. 33, No. 1, pp. 21–31.

Brower et al., "The Synthesis of (4R–cis)–1,1–Dimethylethyl 6–cyanomethyl–2,2–dimethyl–1,3–dioxane–4–acetate, a Key Intermediate for the Preparation of CI–981, a Highly Potent, Tissue Selective Inhibitor of HMG–CoA Reductase", Tetrahedron Letters, vol. 33, No. 17, pp. 2279–2282 (1992).

English Translation of Notification of First Office Action Relating to Chinese Patent Application No. 96195564.3 (Dec. 2000).

English Translation of Response to First Office Action Relating to Chinese Patent Application No. 96195564.3 (Jul. 13, 2001).

English Translation of Response to Telephone Communication Relating to Chinese Patent Application No. 96195564.3 (Dec. 2001).

English Translation of Notification of Granting a Patent Right Relating to Chinese Patent Application No. 96195564.3 (Mar. 2002).

English Translation of Description of Invention Patent Relating to Chinese Patent Application No. 96195564.3 (Jul. 10, 2002)—Cover page and granted claims.

English Translation of Examiner's Report Relating to Czech Republic Patent Application No. PV 1998–121 (Jan. 2002).

English Translation of Reply to Official Letter of Jan. 25, 2002, for Czech Republic Patent Application No. PV 1998–121 (Jun. 2002).

English Translation of Examiner's Report Relating to Czech Republic Patent Application No. PV 1998–121 (Sep. 2002).

English Translation of Reply to Official Letter of Sep. 16, 2002, for Czech Republic Patent Application No. PV 1998–121 (Apr. 2003).

English Translation of Examiner's Report Relating to Czech Republic Patent Application No. PV 1998–121 (Jul. 2003).

English Translation of Reply to Official Letter of Jul. 1, 2003, for Czech Republic Patent Application No. PV 1998–121 (Feb. 2004).

Attachments to Document Previously Submitted as CZ–04 in Information Disclosure Statement Dated Apr. 8, 2005 (English Translation of Reply to Official Letter of Sep. 16, 2002 for Czech Republic Patent Application No. PV 1998–121 (Apr. 2003))—including: (1) Document CZ–07, Attachment (1), Annex 1—Analytical p. 1 of MCD–2540, (2) Document CZ–07, Attachment (2), pp. 1, 2, 3 and 8 of English Language Paper by Isao Sakano et al., "Structure and Absolute Configuration of Atorvastatin Calcium Hydrate" (dated after 1997).

English Translation of Observations of the Patent Office Relating to Ecuador Patent Application No. SP–96–1823 (Jan. 2001).

English Translation of Letter from Patent Office to Applicant Relating to Ecuador Patent Application No. SP–96–1823 (Oct. 21, 1999)—Including translation of Expert's Report on the Application (Sep. 27, 1999).

English Translation of Letter to Patent Office from Applicant Relating to Ecuador Patent Application No. SP–96–1823 (Dec. 15, 1999).

English Translation of Letter to Patent Office from Applicant Concerning Jan. 18, 2001 Observations of Patent Office Relating to Ecuador Patent Application No. SP–96–1823 (No Date).

English Translation of Letter from Patent Office to Applicant Relating to Ecuador Patent Application No. SP–96–1823 (Jun. 4, 2001).

English Translation of Letter to Patent Office from Applicant Relating to Ecuador Patent Application No. SP–96–1823 (Jul. 30, 2001).

English Translation of Letter from Patent Office to Applicant Relating to Ecuador Patent Application No. SP–96–1823 (Sep. 18, 2001).

English Translation of Letter to Patent Office from Applicant Relating to Ecuador Patent Application No. SP–96–1823 (Sep. 27, 2001).

English Translation of Technical Report MCM 06–2002 Relating to Peru Patent Application No. 000539–1966 (Apr. 2002).

English Translation of Brief in Response to Technical Report MCM 06–2002 Relating to Peru Patent Application No. 000539–1996 (Apr. 2002).

English Translation of Submission to Patent Office Relating to Peru Patent Application No. 000539–1996 (Jan. 26, 1998).

English Translation of Notice No. 98–018 Relating to Peru Patent Application No. 000539–1996 (Jan. 30, 1998).

English Translation of Submission of Publication Relating to Peru Patent Application No. 000539–1996 (Mar. 4, 1998).

English Translation of Brief in Response to Technical Report MCM 06–2002 Relating to Peru Patent Application No. 000539–1996 (Sep. 2, 2002)—Rough Translation Previously Submitted as Document PE–02 With Information Disclosure Statement Dated Apr. 8, 2005.

English Translation of Technical Report MCM 06–2002/a Relating to Peru Patent Application No. 000539–1996 (Dec. 10, 2002).

English Translation of New Divisional Application and Comments (Divisional of Peru Patent Application No. 000539–1996 Which Eventually Becomes Peru Patent Application No. 000843–2002) (Aug. 29, 2002).

English Translation of New Divisional Application and Comments (Divisional of Peru Patent Application No. 000539–1996 Which Eventually Becomes Peru Patent Application No. 000844–2002) (Sep. 2, 2002).

English Translation of Examiner's Report Relating to Slovak Republic Patent Application No. PP 0062–98 (Dec. 18, 2003).

English Translation of Response to Official Letter of Dec. 18, 2003 Relating to Slovak Republic Patent Application No. PP 0062–98 (Feb. 13, 2004).

English Translation of Submission by Applicants (Filing of New Text) Relating to Slovak Republic Patent Application No. PP 0062–98 (Jun. 10, 2004).

English Translation of Petition for Independent Amendments and Supplements to the Specification Relating to Taiwan Patent Application No. 85109893 (Nov. 18, 1997)—including set of amended claims.

English Translation of Petition for Independent Supplements to the Specification and a Petition for an Interview Relating to Taiwan Patent Application No. 85109893 (Jun. 23, 1999)—including supplementary specification.

English Translation of Petition for Independent Amendments to the English Specification Relating to Taiwan Patent Application No. 85109893 (Aug. 27, 1999)—Including amended supplementary specification and U.S. package inserts for Lipitor.

English Translation of Response and a Petition for an Interview Relating to Taiwan Patent Application No. 85109893 (Jul. 31, 2000)—Including amended claims and supplementary specification.

English Translation of Independent Supplements to the Specification Relating to Taiwan Patent Application No. 85109893 (Oct. 3, 2000)—including supplementary specification.

English Translation of Petition for Interview and Statement of Interview Relating to Taiwan Patent Application No. 85109893 (Aug. 16, 2001).

English Translation of Response to Interview Held on Aug. 20, 2001 Relating to Taiwan Patent Application No. 85109893 (Sep. 6, 2001))—including: (1) Amended claims; (2) Affidavit of Joel Bernstein; and (3) Copy of Notice of Allowance from Counterpart European Application.

Remaining Attachments to Document Submitted as TW–02 in Information Disclosure Statement Dated Apr. 8, 2005 (English Translation of Reexamination Brief Relating to Taiwan Patent Application No. 85109893—May 1999)—said attachments being: (1) Amended Page of Specification (p. 26); (2) Article, "Atorvastatin Calcium", Drugs of the Future 1997, 22(9): pp. 956–968; (3) Article, "Atorvastatin—A Review of Its Pharmacology and Therapeutic Potential in the Management of Hyperlipidaemias", Adis Drug Evaluation, Drugs 1997 May; 53(5), pp. 829–845; (4) Abstract from Twenty–first Annual ACCP Meeting, 1992, p. 749 No. 28 entitled "Multiple–Dose Tolerance and Pharmacologic Effect of CI–981"; (5) Article, "A Multicenter, Placebo–Controlled, Dose–Ranging Study of Atorvastatin", J. Cardiovasc. Pharmacol. Therapeut. 3(2):119–124, 1998; and (6) Copy of Notice of Allowance for the Counterpart U.S. Appl. No. 08/945,812.

English Translation of Brief Accompanying New Claims and Change of Title Relating to Uruguayan Patent Application No. 24.285 (Apr. 6, 1998).

English Translation (Rough) of Substance of Examiner's Report Dated Oct. 27, 1999 Relating to Uruguayan Patent Application No. 24.285 (Oct. 27, 1999).

English Translation of Reply to Examiner's Report Relating to Uruguayan Patent Application No. 24.285 (Mar. 20, 2000).

English Translation of Attachments to Document Submitted with Information Disclosure Statement Dated Apr. 8, 2005 as UR–02 (English Translation of Examination Report for Uruguayan Patent Application No. 24.985 dated Aug. 12, 2002)—Including: (1) Document UR–08, Attachment (1), English Translation of Substance of Amended Specification and Claims Pages, (2) Document UR–08, Attachment (2), Annex 1—Analytical Page 1 of MCD–2540, (3) Document UR–08, Attachment (3), English Language Paper by Isao Sakano et al., "Structure and Absolute Configuration of Atorvastatin Calcium Hydrate" (dated after 1997), (4) Document UR–08, Attachment (4), English Language Article by Kelvin L. Baumann et al., "The Convergent Synthesis of CI–981, an Optically Active, Highly Potent, Tissue Selective Inhibitor of HMG–CoA Reductase", Tetrahedron Letters, vol. 33, No. 17, 1992, pp. 2283–2284.

English Translation of Reply to Official Action Attaching a New Set of Claims, New Abstract and New Title Relating to Uruguayan Patent Application No. 24.985 (Dec. 30, 2002).

English Translation of Reply to Official Action Attaching a New Set of Claims Relating to Uruguayan Patent Application No. 24.985 (Feb. 13, 2003).

English Translation of Reply to Official Action of May 26, 1998 for Israel Patent Application No. 122118 (Sep. 15, 1998).

English Translation of Letter from Israel PTO to Applicant Relating to Israel Patent Application No. 122118 (Dec. 28, 1998).

English Translation of Letter from Israel PTO to Applicant Relating to Israel Patent Application No. 122118 (Mar. 2, 1999).

English Translation of Letter from Applicant to Israel PTO Relating to Israel Patent Application No. 122118 (Jul. 12, 1999).

English Translation of Letter From Opponent Unipharm Ltd. to Israel PTO Relating to Israel Patent Application No. 122118 (Oct. 14, 1999).

English Translation of Information Disclosure Update Relating to Israel Patent Application No. 122118 (Apr. 4, 2000).

English Translation of Letter from Israel PTO to Applicant Relating to Israel Patent Application No. 122118 (May 14, 2002).

English Translation of Letter from Applicant to Israel PTO Relating to Israel Patent Application No. 122118 (May 13, 2003)—including marked–up and clean copies of pages of specification and claims.

English Translation of Letter from Israel PTO to Applicant Relating to Israel Patent Application No. 122118 (Dec. 28, 2003).

English Translation of Letter from Applicant to Israel PTO Relating to Israel Patent Application No. 122118 (May 20, 2004)—including amended p. 31.

English Translation of Letter from Israel PTO to Applicant Relating to Israel Patent Application No. 122118 (Jun. 28, 2004).

English Translation of Letter from Applicant to Israel PTO Relating to Israel Patent Application No. 122118 (Apr. 17, 2005)—including amended p. 31.

English Translation of Letter from Israel PTO to Applicant Relating to Israel Patent Application No. 128862 (Jul. 19, 1999)—including marked–up pages of specification and claims.

English Translation of Letter from Applicant to Israel PTO Relating to Israel Patent Application No. 128862 (Nov. 16, 1999).

English Translation of Interview Summary Relating to Israel Patent Application No. 128862 (Oct. 12, 2004).

English Translation of Letter from Applicant to Israel PTO Relating to Israel Patent Application No. 128862 (Oct. 17, 2004)—including new set of claims.

English Translation of Letter from Applicant to Israel PTO Relating to Israel Patent Application No. 128862 (Oct. 24, 2004)—including new set of claims.

English Translation of Letter from Israel PTO to Applicant Relating to Israel Patent Application No. 128862 (Oct. 25, 2004).

English Translation of Letter from Israel PTO to Applicant Relating to Israel Patent Application No. 128862 (Nov. 4, 2004).

English Translation of Letter from Applicant to Israel PTO Relating to Israel Patent Application No. 128862 (Nov. 7, 2004).

Declaration of Joel Bernstein dated Dec. 8, 2004 and Affidavit of Joel Bernstein dated Nov. 2, 2000—submitted as attachments to Document IL–05 from Information Disclosure Statement dated Apr. 8, 2005 (IL–05=English Translation of Letter Filed Mar. 4, 2005 in Response to Official Action of Nov. 4, 2004 Concerning Israel Patent Application No. 128862—mistakenly referred to as 128864 in Information Disclosure Statement dated Apr. 8, 2005).

English Translation of Letter from Israel PTO to Applicant Relating to Israel Patent Application No. 128865 (Jul. 19, 1999).

English Translation of Letter from Applicant to Israel PTO Relating to Israel Patent Application No. 128865 (Dec. 6, 1999)—including Memorandum in Response to Official Action; citation of prior art and amended pages of specification.

English Translation of Letter from Israel PTO to Applicant Relating to Israel Patent Application No. 128865 (Apr. 10, 2000).

English Translation of Letter from Israel PTO to Applicant Relating to Israel Patent Application No. 128865 (Aug. 9, 2004)—including marked–up pages of specification and claims.

English Translation of Interview Summary Relating to Israel Patent Application No. 128865 (Oct. 12, 2004).

English Translation of Letter from Applicant to Israel PTO Relating to Israel Patent Application No. 128865 (Dec. 9, 2004)—including amended pages of specification and claims.

English Translation of Letter from Israel PTO to Applicant Relating to Israel Patent Application No. 128864 (Jul. 19, 1999).

English Translation of Letter from Applicant to Israel PTO Relating to Israel Patent Application No. 128864 (Sep. 14, 1999)—including Memorandum in Response to Official Action and amended pages of specification and claims.

English Translation of Letter from Applicant to Israel PTO Relating to Israel Patent Application No. 128864 (Dec. 2, 1999)—including Memorandum in Response to Official Action.

English Translation of Letter from Israel PTO to Applicant Relating to Israel Patent Application No. 128864 (Apr. 10, 2000).

English Translation of Letter from Applicant to Israel PTO Relating to Israel Patent Application No. 128864 (Apr. 10, 2000).

English Translation of Letter from Israel PTO to Applicant Relating to Israel Patent Application No. 128864 (Aug. 9, 2004)—including marked–up versions of pages of the specification and claims.

English Translation of Interview Summary Relating to Israel Patent Application No. 128864 (Oct. 12, 2004).

English Translation of Letter from Applicant to Israel PTO Relating to Israel Patent Application No. 128864 (Dec. 9, 2004)—including amended pages of specification and claims.

English Translation of Letter from Israel PTO to Applicant Relating to Israel Patent Application No. 128864 (Jan. 17, 2005)—including marked–up version of pages from specification and claims.

Request to Hold Application in Abeyance Relating to New Zealand Patent Application No. 312907 (Dec. 21, 1999).

Examination Report Relating to New Zealand Patent Application No. 312907 (Jan. 20, 2000).

Application for Amendment to Specification of New Zealand Patent Application No. 312907 (Oct. 27, 2000).

Attachments to Document Previously Submitted as NZ–02 in Information Disclosure Statement dated Apr. 8, 2005—Response with Amendments to New Zealand Patent Application No. 312907 (Oct. 27, 2000)—the attachments being: (1) Copy of U.S. Pat. No. 5,969,156; (2) Kohn et al., J. Med. Chem 1990, vol. 33, No. 3, pp. 919–926; (3) Poindexter et al., J. Org. Chem. 1992, vol. 57, No. 23, pp. 6257–6265; (4) Crocker et al., Bioconjugate Chem. vol. 1, No. 6, 1990, pp. 419–424; and (5) U.S. Pat. No. 5,378,729 (Kohn et al.).

Examination Report Relating to New Zealand Patent Application No. 312907 (Nov. 9, 2000).

Notice of Acceptance of Complete Specification Relating to New Zealand Patent Application No. 312907 (Nov. 27, 2000).

Copy of Letters Patent No. 312907 (cover page) Relating to New Zealand Patent Application No. 312907 (Apr. 5, 2001).

Examination Report Relating to New Zealand Patent Application No. 507836 (Divisional of 312907) (Nov. 2, 2000).

Response to Examination Report Relating to New Zealand Patent Application No. 507836 (Divisional of 312907) (Jan. 23, 2001).

Examination Report Relating to New Zealand Patent Application No. 507836 (Divisional of 312907) (Jan. 29, 2001).

Notice of Acceptance of Complete Specification Relating to New Zealand Patent Application No. 507836 (Divisional of 312907) (Feb. 8, 2001).

Copy of Letters Patent No. 507836 (cover page) Relating to New Zealand Patent Application No. 507836 (Divisional of 312907) (Jun. 6, 2001).

English Translation of Examination Report Relating to Colombian Patent Application No. 96–037.514 (Technical Section Report No. 447) (Mar. 2001).

English Translation of Observations on the Technical Section Report No. 447 Relating to Colombian Patent Application No. 96–037.514 (Mar. 2001).

English Translation of Main Parts of Technical Section Report No. 1680 Relating to Colombian Patent Application No. 96–037.514 (Nov. 20, 2001).

English Translation of Technical Section Report No. 1647 Relating to Colombian Patent Application No. 96–037.514 (Jan. 2003).

English Translation of Testimony Reception Proceeding of Dr. Jose Antonio Henao Martinez Relating to Colombian Patent Application No. 96–037.514 (Jul. 2004).

English Translation of Brief in Response to Technical Concept No. 0151 Relating to Colombian Patent Application No. 96–037.514 (Jul. 19, 2001) with the following attachments: (1) Cover page and pp. 3–12 of book "Solid–State Chemistry of Drugs", Stephen R.Byrn, Academic Press 1982; (2) Article by Robert J. Gdanitz; "Ab initio prediction of molecular crystal structures"; Current Opinion in Solid State & Materials Science 1998, 3: pp. 414–418; (3) Article by Mino R. Caira; "Crystalline Polymorphism of Organic Compounds"; Topics in Current Chemistry, vol. 198, 1998, pp. 163–208; (4) Article by Gautam R. Desiraju; "Crystal Gazing: Structure Prediction and Polymorphism"; Science, vol. 278; Oct. 17, 1997, pp. 404–405; (5) Copy of English Translation of WO 01/28999 (PCT/HU00/00106)(Apr. 26, 2001); (6) Copy of Cover Pages for Argentine Patent AR003458B1; (7) Copy of Cover Page for Australian Patent No. 725424; (8) Copy of Cover Page for Canadian Patent No. 2,220,018;

(9) Copy of Cover Page for Chilean Patent No. 39.996; (10) Copy of Cover Page for Indonesian Patent No. ID 0004715; (11) Copy of Cover Page for New Zealand Patent Nos. 507836 and 312907; (12) Copy of Cover Pages for Norway Patent No. 309898; (13) Copy of Cover Page for Eurasian Patent No. 000474; (14) Copy of Cover Page for Vietnam Patent No. 1507; and (15) Copy of English Translation of Letter Issued by the Intellectual Property Autonomous Service and New Technologies of Venezuela Relating to the Grant of a Patent from Venezuelan Patent App. No. 96–001279 (Feb. 19, 2001).

English Translation of Resolution No. 40899 Relating to Colombian Patent Application No. 96–037.514 (Nov. 30, 2001).

English Translation of Reconsideration Petition Against Resolution 40899 Relating to Colombian Patent Application No. 96–037.514 (Jan. 24, 2002)—including an Affidavit of Stephen R. Byrn dated Jan. 21, 2002 (Attachment (1)).

English Translation of Complementing Brief Relating to Colombian Patent Application No. 96–037.514 (Oct. 22, 2002)—including: Attachment (1)—Affidavit of Joel Bernstein dated Nov. 2, 2000; Attachment (2)—Result of Consultation by Telephone in European Application No. 96 924 368.2 (Apr. 13, 2000).

English Translation of Resolution No. 060 Relating to Colombian Patent Application No. 96–037.514 (Jan. 14, 2003).

English Translation of Nullity Claim Against Resolution Nos. 40899 and 060 Relating to Colombian Patent Application No. 96–037.514 (2003)—including: Attachment (1)—Declaration of Stephen R. Byrn (Jun. 6, 2003); Attachment (2)—Affidavit of Stephen R. Byrn (Jan. 21, 2002); Attachment (3)—Cover Pages, Table of Contents, Author Index, Notice to Authors and Article by Leo H. Sternbach; "The Benzodiazepine Story"; pp. 1–7; all from the Journal of Medicinal Chemistry, vol. 22, No. 1, Jan. 1979; Attachment (4)—Affidavit of Charles E. Colson (Sep. 2002); and Attachment (5)—Affidavit of Lloyd R. Whitfield (Sep. 2002).

English Translation of Preliminary Letter from Patent Office Relating to Bulgarian Patent Application No. 102187 (Oct. 10, 2001).

English Translation of Response to Preliminary Letter from Patent Office Relating to Bulgarian Patent Application No. 102187 (Jan. 18, 2002)—including replacement pages for description and abstract.

English Translation of Further Response to Preliminary Letter from Patent Office Relating to Bulgarian Patent Application No. 102187 (Mar. 7, 2002)—including replacement pages for description.

English Translation of Examiner's Report No. 2 Relating to Chilean Patent Application No. 1264–96 (Aug. 1998).

English Translation of Examiner's Report No. 3 Relating to Chilean Patent Application No. 1264–96 (Jun. 1999).

English Translation of First Examiner's Report Relating to Chilean Patent Application No. 1264–96 (Apr. 8, 1998).

English Translation of Reply to Examiner's Report No. 1 and Accompanying Antecedents Relating to Chilean Patent Application No. 1264–96 (Jun. 9, 1998).

English Translation of Submission of Substitute p. 31 to Patent Office Relating to Chilean Patent Application No. 1264–96 (Jul. 9, 1998).

English Translation of Examiner's Report No. 2 Relating to Chilean Patent Application No. 1264–96 (Aug. 13, 1998)—Rough Translation Previously Submitted as Document CL–01 in Information Disclosure Statement Dated Apr. 8, 2005.

English Translation of Reply to Examiner's Report No. 2 and Filing of Antecedents Relating to Chilean Patent Application No. 1264–96 (Mar. 1999).

English Translation of Examiner's Report No. 3 Relating to Chilean Patent Application No. 1264–96 (Jun. 2, 1999)—Rough Translation Previously Submitted as Document CL–02 in Information Disclosure Statement Dated Apr. 8, 2005.

English Translation of Reply to Examiner's Report No. 3 and Accompanying Antecedents Relating to Chilean Patent Application No. 1264–96 (Jun. 10, 1999).

English Translation of Examiner's Report No. 4—Final Acceptance of Application—Relating to Chilean Patent Application No. 1264–96 (Jun. 11, 1999).

Examination Report Relating to Australian Patent Application No. 64842/96 (Nov. 1998).

Response to the Examination Report of Nov. 1998 Relating to Australian Patent Application No. 64842/96 (Aug. 2000).

Attachments to document AU–02 submitted with Information Disclosure Statement dated Apr. 8, 2005 (Response to the Examination Report of Nov. 1998 Relating to Australian Patent Application No. 64842/96 (Aug. 2000))—such attachments being: (1) Declaration of Lloyd R. Whitfield; (2) Declaration of Charles Edward Colson; (3) Kohn et al., J. Med. Chem 1990, vol. 33, No. 3, pp. 919–926; (4) Poindexter et al., J. Org. Chem. 1992, vol. 57, No. 23, pp. 6257–6265; (5) Crocker et al., Bioconjugate Chem. vol. 1, No. 6, 1990, pp. 419–424; and (6) U.S. Pat. No. 5,378,729 (Kohn et al.).

Statement of Proposed Amendments Relating to Australian Patent Application No. 64842/96 (Aug. 17, 2000).

Notice of Acceptance Relating to Australian Patent Application No. 64842/96 providing Australian Patent No. 725424 (Oct. 3, 2000).

Notice of Sealing (Grant of Patent) Relating to Australian Patent Application No. 64842/96 (Australian Patent No. 725424) (Jan. 25, 2001).

English Translation of Amendment to the Claims Relating to South Korean Patent Application No. 10–1998–700346 (Oct. 30, 1999).

English Translation of Notice of Preliminary Rejection Relating to South Korean Patent Application No. 10–1998–700346 (Oct. 30, 2001).

English Translation of Response to Office Action Relating to South Korean Patent Application No. 10–1998–700346 (Dec. 24, 2002)—Including Affidavit of Park, Man–Ki (Dec. 11, 2002) and Affidavit of Joel Bernstein (Nov. 2, 2000).

English Translation of Amendment of the Application Relating to South Korean Patent Application No. 10–1998–700346 (Dec. 24, 2002).

English Translation of Notice of Allowance Relating to South Korean Patent Application No. 10–1998–700346 (May 2, 2003).

English Translation of Patent Publication Relating to South Korean Patent Application No. 10–1998–700346; Patent No. 10–389518 (Nov. 15, 2003).

English Translation of Divisional Patent Application filing sheet—including claims (South Korean Patent Application No. 10–2002–7017608) (Dec. 24, 2002).

English Translation of Notice of Preliminary Rejection Relating to Divisional Patent Application (South Korean Patent Application No. 10–2002–7017608) (May 17, 2003).

English Translation of Response to Office Action Relating to Divisional Patent Application (South Korean Patent Application No. 10–2002–7017608) (Sep. 17, 2003).

English Translation of Amendment to the Claims Relating to Divisional Patent Application (South Korean Patent Application No. 10–2002–7017608) (Sep. 17, 2003).

English Translation of Notice of Allowance Relating to Divisional Patent Application (South Korean Patent Application No. 10–2002–7017608) (Mar. 17, 2004).

English Translation of Patent Publication Relating to Divisional Patent Application (South Korean Patent Application No. 10–2002–7017608; Patent No. 10–431038) (May 12, 2004).

English Translation of Patent Office Resolution I–396 Relating to Argentine Patent Application No. 96 01 03598 (Oct. 1999).

English Translation of Answer to Official Action Relating to Argentine Patent Application No. 96 01 03598 (Jul. 2000).

English Translation of Answer to Official Action Relating to Argentine Patent Application No. 96 01 03598 (Jul. 24, 2000)—with the following attachments: (1) Certified and Legalized Copy of U.S. Pat. No. 5,969,156; (2) Legalized Copy of Affidavit of Tanya R. McMullen (Dec. 17, 1999) with attachments: (a) Declaration of Thomas M.A. Bocan (Dec. 2, 1998); (b) Declaration of Stephen R. Byrn (Nov. 25, 1998); (c) Declaration of Lloyd R. Whitfield (Dec. 2, 1998); and (d) Declaration of Charles Edward Colson (Dec. 2, 1998) (3) Legalized Affidavit of Francis J. Tinney enclosing Notice of Allowance for U.S. Appl. No. 08/945,812 (Dec. 17, 1999); (4) Affidavit of Bruce D. Roth (Dec. 17, 1999); (5) Kohn et al., J. Med. Chem 1990, vol. 33, No. 3, pp. 919–926; (6) Poindexter et al., J. Org. Chem. 1992, vol. 57, No. 23, pp. 6257–6265; (7) Crocker et al., Bioconjugate Chem. vol. 1, No. 6, 1990, pp. 419–424; (8) U.S. Pat. No. 5,378,729 (Kohn et al.);

(9) English translation of Notice of Receipt of Invention Application 122118 (Israel); (10) English translation of Technical Expert's Report Concerning a Patent Application (Ecuador App. No. SP–96–1823) (Sep. 27, 1999); (11) Copy of International Search Report for WO 97/03959 (Feb. 6, 1997); (12) English translation of Certificate of Chilean Patent No. 39996 (Jul. 1, 1999); (13) Bocan et al., Atherosclerosis 111 (1994), pp. 127–142; (14) English translation of new set of claims for Argentine Pat. App. P 96 01 03598; and (15) English translation of Filing of Documents Related to the Answer to the Substantive Examination of Patent Application Serial No. P 96 01 03598 (Oct. 2000)—including a copy of Indonesian Patent ID 0004715. (Document AR–03 is a more complete translation of the document submitted, without most of the attachments, as AR–02 in Information Disclosure Statement dated Apr. 8, 2005).

English Translation of Opposition to the Granting of Exclusive Marketing Rights Relating to Argentine Patent No. AR 003458 (corresponding to Application No. P 96 01 03598) Filed by GADOR (Jun. 25, 1999).

English Translation of Opposition to the Granting of Exclusive Marketing Rights Relating to Argentine Patent No. AR 003458 (corresponding to Application No. P 96 01 03598), Filed by LABORATORIOS BETA S.A. (Jun. 24, 1999).

English Translation of Opposition to the Granting of Exclusive Marketing Rights Relating to Argentine Patent No. AR 003458 (corresponding to Application No. P 96 01 03598) Filed by ASOFARMA S.A. (Jun. 24, 1999).

English Translation of Opposition to the Granting of Exclusive Marketing Rights Relating to Argentine Patent No. AR 003458 (corresponding to Application No. P 96 01 03598) Filed by MICROSULES Y BERNABO SA (Jun. 25, 1999).

English Translation of Substantive Examination Report Relating to Argentine Patent Application No. P 96 01 03598 (Aug. 11, 1999).

Exclusive Marketing Rights for LIPITOR® In Argentina (Dec. 14, 1999)—A Summary of Argentina's Failure to Grant Exclusive Marketing Rights for LIPITOR®—including the following Annexes: (1) TRIPS Article 70, paragraph 9, and Article 101 of Argentine Decree 260/96 and the Associated Regulation; (2) Application for Exclusive Marketing Rights (Jun. 9, 1998); (3) INPI Technical Resolution (Nov. 18, 1998); (4) INPI Legal Resolution (Dec. 2, 1998); (5) Warner–Lambert's Response (Dec. 15, 1998); (6) INPI Legal Resolution (Feb. 11, 1999); (7) INPI Technical Resolution (Apr. 21, 1999); (8) INPI's Brief Before the Court of First Instance in the Amparo; (9) Notice of the Application of Exclusive Marketing Rights; (10) Warner–Lambert's Response to the Oppositions Filed; (11) INPI's Brief on Appeal in the Amparo; (12) Warner–Lambert's Brief on Appeal in the Amparo;

(13) Communication from INPI Legal Affairs to the Interventor About the Decision in the Amparo (Oct. 13, 1999); (14) Acknowledgement by the Interventor of the Decision in the Amparo (Oct. 13, 1999); (15) Transmittal of the Examiner's Action (Oct. 14, 1999); and (16) INPI Resolution Refusing the Application for Exclusive Marketing Rights (Oct. 20, 1999).

W. Thellhelmer, *Synthetic Methods of Organic Chemistry*, vol. 13, Interscience Publishers, Inc., New York, cover pages and pp. 193, 194, 383 and 384 (1959).

Shimako Oishi et al.; *A Clinical Study of the Pharmacokinetics of Atorvastatin (CI–981), I: The Relative Bioavailabilities of Amorphous and Crystalline Atorvastatin Preparations*, Jpn Pharmacol Ther, vol. 26, No. 8, pp. 67–77 (1241–1251) (1998).

English language translation of Shimako Oishi et al.; *A Clinical Study of the Pharmacokinetics of Atorvastatin (CI–981), I: The Relative Bioavailabilities of Amorphous and Crystalline Atorvastatin Preparations*, Jpn Pharmacol Ther, vol. 26, No. 8, pp. 67–77 (1241–1251) (1998).

Request for Advanced Examination (Special Order) for Canadian Patent Application No. 2,220,018 (Mar. 2000).

Office Action dated Jul. 5, 2000 Relating to Canadian Patent Application No. 2,220,018 (Jul. 2000).

Response and Amendment to the Office Action dated Jul. 5, 2000, for Canadian Patent Application No. 2,220,018 (Nov. 2000).

Voluntary Amendment and Notice of Allowance for Canadian Patent Application No. 2,220,018 (Nov. 2000).

Notice of Allegation filed by Ranbaxy in Canada (Jan. 31, 2005)—including discussion of '018 patent at pp. 32 to 37.

Notice of Allegation filed by Novopharm in Canada (Feb. 22, 2005)—including discussion of '018 patent at pp. 16 to 25.

Notice of Application filed by Pfizer in Canada Relating to Ranbaxy Notice of Allegation (Mar. 17, 2005)—including discussion of '018 patent at pp. 11 and 12.

Notice of Application filed by Pfizer in Canada Relating to Novopharm Notice of Allegation (Apr. 13, 2005)—including discussion of '018 patent at pp. 11 to 15.

Notice of Allegation filed by Ratiopharm in Canada (May 12, 2005)—including discussion of '018 patent at pp. 22 to 36.

Notice of Application filed by Pfizer in Canada Relating to Ratiopharm Notice of Allegation (Jun. 30, 2005)—Including discussion of '018 patent at pp. 10 to 15.

Official Action dated Dec. 10, 1999 Concerning European Patent Application 96 924 368.2.

Result of Consultation dated Apr. 19, 2000 Concerning European Patent Application 96 924 368.2.

Response to Communication of Sep. 20, 2000 European Patent Application 96 924 368.2 (document dated Nov. 4, 2000).

Communication of Apr. 12, 2001 European Patent Application 96 924 368.2.

Response to the Communication Pursuant to Article 96(2) dated Apr. 12, 2001 European Patent Application 96 924 368.2 (May 2001).

Communication under Rule 51(4) EPC dated Jul. 26, 2001 European Patent Application 96 924 368.2.

Response to the Communication Under Rule 51(4) EPC dated Jul. 26, 2001 European Patent Application 96 924 368.2 (Aug. 2001).

Communication Under Rule 51(6) EPC dated Sep. 21, 2001 European Patent Application 96 924 368.2.

Decision to Grant a European Patent Pursuant to Article 97(2) EPC dated Sep. 27, 2001 European Patent Application 96 924 368.2.

Communication of Notice of Opposition Dated Aug. 13, 2002 European Patent Application 96 924 368.2; in German (Opposing Party=Dr. Robert Waldraff) and English Translation of Communication.

Communication of a Notice of Opposition Dated Aug. 16, 2002 European Patent Application 96 924 368.2 (Opposing Part=Teva Pharmaceutical Industries Ltd..).

Communication of a Notice of Opposition Dated Aug. 20, 2002 European Patent Application 96 924 368.2 (Opposing Part=Lek Pharmaceuticals d.d.).

Response to the Communication of Notices of Oppositions European Patent Application 96 924 368.2; dated May 12, 2003.

Reply by Opponent Dr. Robert Waldraff to the Submission filed by patentee dated May 12, 2003 European Patent Application 96 924 368.2 (Nov. 2003).

Communication from EPO Dated Dec. 7, 2004 European Patent Application 96 924 368.2.

Response to Communication in Oppositions Concerning European Patent Application 96 924 368.2 (Jul. 18, 2005)—including SSCI Inc. Report (Filename SR–20030653.01—10 pages) and Filtration and Drying Study (1 page).

English Translation of Court Claim filed on Jul. 15, 2005, with the Metropolitan Court of Budapest, Hungary—including a copy of Hungarian Patent No. 223 599.

English Translation of Declaration filed on Aug. 16, 2005, with the Metropolitan Court of Budapest, Hungary—including a copy of SSCI Inc. Report (Filename SR–20050594.01).

English language version of Response by Dr. Judith Aronhime dated Sep. 20, 2005 for Presentation in the Metropolitan Court of Budapest, Hungary.

English Translation of Written Request for Examination of Japanese Patent Application No. H09(1997)–506710 (Feb. 16, 2000).

English Translation of Written Amendment for Japanese Patent Application No. H09(1997)–506710 (Feb. 16, 2000).

English Translation of Notice of Reason(s) for Rejection for Japanese Patent Application No. H09(1997)–506710 (Jul. 17, 2001).

English Translation of Written Request for Extension of Term—Japanese Patent Application No. H09(1997)–506710 (Oct. 17, 2001).

English Translation of Written Amendment In Lieu of Written Opinion for Japanese Patent Application No. H09(1997)–506710 (Jan. 17, 2002).

English Translation of Copy of Decision For Patent for Japanese Patent Application No. H09(1997)–506710 (Mar. 5, 2002).

English Translation of Letters Patent Document (Patent No. 3296564) for Japanese Patent Application No. H09(1997)–506710 (Apr. 12, 2002).

English Translation of Claim for Patent Violation Against Ranbaxy (Dec. 10, 2003).

English Translation of Technical Report mcm 1–2004/a Submitted in Ranbaxy Litigation (Feb. 11, 2004).

English Translation of Ranbaxy Answer (Mar. 2, 2004)—with the following attachments: Attachment 1—English Translation of Technical Report No. 009/04/L. Attachment 2—English Translation of Quality Control Service Test Report No. P014695A/02, Attachment 3—English Translation of Letter from Hypatia S.A. dated Jul. 16, 2002.

English Translation of Technical Report mcm 1–2004/c (Jun. 8, 2004).

English Translation of Decision by INDECOPI (Jun. 8, 2004).

English Translation of Appeal for Reversal of Precautionary Measures filed by Ranbaxy (Jun. 24, 2004).

English Translation of Resolution No. 0793–2004/TPI–IN-DECOPI (Sep. 7, 2004).

English Translation of Technical Report MCM 1–2004/D (Oct. 22, 2004).

English Translation of Resolution No. 001270–2004/OIN-INDECOPI (Oct. 26, 2004).

English Translation of Filing of an Appeal by Ranbaxy (Nov. 5, 2004).

English Translation of Answer to the Action for Annulment filed by Warner–Lambert (Aug. 11, 2005).

English Translation of Complaint Filed by VIVAX to the Andean Secretary General in 2004 Concerning Venezuelan Patent No. 96–001279 (Cancellation Proceedings).

Expert Opinion of Bernardo Mendez A., Ph.D. in Spanish dated Apr. 27, 2004 submitted in Cancellation Proceedings Concerning Venezuelan Patent No. 96–001279 and English Translation Thereof.

Expert Opinion of Jose Dominguez, Ph.D. In Spanish dated Aug. 33, 2004 Submitted in Cancellation Proceedings Concerning Venezuelan Patent No. 96–001279 and English Translation Thereof.

English Translation of Action for Breach filed by VIVAX in Andean Community's Court of Justice (Sep. 24, 2004).

English Translation of Response to VIVAX Action for Breach filed by Warner–Lambert in Andean Community's Court of Justice (Dec. 17, 2004).

English Translation of Written Conclusions Submitted by Warner–Lambert to Andean Community's Court of Justice Relating to VIVAX Action (May 13, 2005), including the following Annexes: Annex A—Document from Colombia relating to the patentability of polymorphs (no translation), Annexes B, C and D—Excerpts from "Solid State Chemistry of Drugs, $2^{nd}$ Edition", Byrn et al. (1999) (Cover pages and pp. 4, 5, 12, 13, 248 and 249). Annexes E and F—Excerpts from "Polymorphism in Molecular Crystals", Joel Bernstein, IUCr Monographs on Crystallography (14), Clarendon Press, Oxford (2002) (Cover pages and pp. 8–11, 240 and 241). Annex G—Table concerning support for claims, Annex H—Certified copy of public document relating to Colombian process patent for amorphous atorvastatin, Annex I—Power Point presentation of Expert Professor Jose Miguel Delgado Q., presented at the Court of Justice of the Andean Community of Nations (May 5, 2005) and English Translation thereof.

English Translation of Notification of Proposal to Revoke Patent No. 3270 (should be Patent No. 1507) (Jun. 20, 2005) with attached Proposal to a Revocation of Patent No. 1507 (Mar. 21, 2005).

English Translation of Examination Report for Uruguayan Patent Application No. 24.985 dated May 2002.

English Translation of Reply to Examination Report for Uruguayan Patent Application No. 24.985 dated Aug. 12, 2002.

English Translation of Examination Report for Uruguayan Patent Application No. 24.985 dated Sep. 2002.

English Translation of Examination Report for Uruguayan Patent Application No. 24.985 dated Jan. 2003.

English Translation of Official Notification Relating to Taiwan Patent Application No. 85109893 (Oct. 1998).

English Translation of Reexamination Brief Relating to Taiwan Patent Application No. 85109893 (May 1999).

English Translation of Preliminary Notice of Rejection Relating to Taiwan Patent Application No. 85109893 (May 2000).

English Translation of Preliminary Notice of Rejection Relating to Taiwan Patent Application No. 85109893 (Apr. 2001).

English Translation of Examiner's Grounds for Rejection Relating to South Korean Patent Application No. 10–1998–700346 (Oct. 2001).

Examiner's Report Relating to New Zealand Patent Application No. 312907 (Jun. 1998).

Response with Amendments to New Zealand Patent Application No. 312907 (Oct. 2000).

English Translation of Reply to Official Action of Dec. 28, 1998 for Israel Patent Application No. 122118; dated Mar. 1, 1999.

English Translation of Statement of Case on Behalf of Opponent Unipharm Ltd. Dated Feb. 8, 2000; Opposition to Israel Patent Application No. 122188.

English Translation of Request to Amend the Specification of Israel Patent Application No. 122118; dated Oct. 2000.

English Translation of Additions to Statement of Case; Unipharm Ltd. Opposition to Israel Patent Application No. 122118; dated Sep. 11, 2002.

English Translation of Letter Filed Mar. 4, 2005 in Response to Official Action of Nov. 4, 2004 Concerning Israel Patent Application No. 128864.

* cited by examiner

US 5,969,156 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 3, 6–8, 14–15, 20–25, 30, 32–35, 37 and 39–44 is confirmed.

Claims 1–2, 4–5, 9, 28–29, 31, 36 and 38 are determined to be patentable as amended.

Claims 10–13, 16–19 and 26–27, dependent on an amended claim, are determined to be patentable.

New claims 45–117 are added and determined to be patentable.

1. A crystalline Form I atorvastatin hydrate having an X-ray powder diffraction containing [at least one of] the following 2θ [values] *value* measured using $CuK_\alpha$ radiation: [11.9 or] 22.0.

2. A crystalline Form I atorvastatin hydrate having an X-ray powder diffraction containing the following 2θ values measured using [$Cuk_\alpha$] $CuK_\alpha$ radiation: 11.9, 21.6 and 22.0.

4. A crystalline Form I atorvastatin hydrate having an X-ray powder diffraction containing the following 2θ values measured using [$Cuk_\alpha$] $CuK_\alpha$ radiation: 9.2, 9.5, 10.3, 10.6, 11.9, 12.2, 17.1, 19.5, 21.6, 22.0, 22.7, 23.3, 23.7, 24.4, 28.9 and 29.2.

5. A crystalline Form I atorvastatin hydrate having an X-ray powder diffraction containing the following 2θ values measured using [$Cuk_\alpha$] $CuK_\alpha$ radiation: 9.150, 9.470, 10.266, 10.560, 11.853, 12.195, 17.075, 19.485, 21.626, 21.960, 22.748, 23.335, 23.734, 24.438, 28.915 and 29.234.

9. A crystalline Form I atorvastatin hydrate characterized by solid-state $^{13}C$ nuclear magnetic resonance having the following chemical shifts expressed in parts per million: 21.3[*,*], 25.2, 26.4, 40.2, 41.9, 47.4, 64.9, 68.1, 70.5, 73.1, 113.8, 118.2, 120.9, 123.5, 127.6, 129.5, 131.1, 134.9, 137.0, 159.3, 166.7, (broad), 178.4 and 182.8.

28. Crystalline Form II atorvastatin or a hydrate thereof having an X-ray powder diffraction containing the following 2θ values measured using $CuK_\alpha$ radiation: 9.0 [and], 20.5 *and at least one value selected from the group consisting of 5.6, 7.4, 8.5, 15.8 (broad) and 25.7 (broad)*.

29. Crystalline Form II atorvastatin or a hydrate thereof having an X-ray powder diffraction containing the following 2θ values measured using $CuK_\alpha$ radiation: 8.5 [and], 9.0 *and at least one value selected from the group consisting of 7.4, 12.4 (broad), 15.8 (broad), 17.1–17.4 (broad), 19.5, 20.5, 22.7–23.2 (broad) and 25.7 (broad)*.

31. Crystalline Form II atorvastatin or a hydrate thereof having an X-ray powder diffraction containing the following 2θ values measured using [$Cuk_\alpha$] $CuK_\alpha$ radiation: 5.582, 7.384, 8.533, 9.040, 12.440 (broad), 15.771 (broad), 17.120–17.360 (broad), 19.490, 20.502, 22.706–23.159 (broad), 25.697 (broad) and 29.504.

36. Crystalline Form IV atorvastatin or a hydrate thereof having an X-ray powder diffraction containing [at least one of] the following 2θ values measured using $CuK_\alpha$ radiation: 8.0 [or], 9.7 *and at least one value selected from the group consisting of 4.9, 5.4, 10.4, 12.4, 18.4, 19.2, 21.7, 23.0 and 24.1*.

38. Crystalline Form IV atorvastatin or a hydrate thereof having an X-ray powder diffraction containing the following 2θ values measured using $CuK_{60}$ radiation: 8.0, 9.7 [and], 19.6 *and at least one value selected from the group consisting of 4.9, 5.4, 10.4, 12.4, 18.4, 19.2, 21.7, 23.0 and 24.1*.

*45. A crystalline Form I atorvastatin hydrate having an X-ray powder diffraction containing the following 2θ values measured using $CuK_\alpha$ radiation: 11.9 and 22.0.*

*46. Crystalline Form IV atorvastatin or a hydrate thereof having an X-ray powder diffraction containing the following 2θ values measured using $CuK_\alpha$ radiation: 8.0 and at least one value selected from the group consisting of 4.9, 5.4, 10.4, 12.4, 18.4, 19.2, 21.7, 23.0 and 24.1.*

*47. A crystalline Form I atorvastatin hydrate having an X-ray powder diffraction containing the following 2θ values measured using $CuK_\alpha$ radiation: 17.1, 19.5, 21.6 and at least one value selected from the group consisting of 9.2, 10.3, 11.9, 12.2, 22.0, 22.7, 23.7, 24.4, 28.9 and 29.2.*

*48. Crystalline Form IV atorvastatin or a hydrate thereof having an X-ray powder diffraction containing the following 2θ values measured using $CuK_\alpha$ radiation: 8.0 and 12.4.*

*49. Crystalline Form IV atorvastatin or a hydrate thereof having an X-ray powder diffraction containing the following 2θ values measured using $CuK_\alpha$ radiation: 8.0, 9.7 and 12.4.*

*50. Crystalline Form IV atorvastatin or a hydrate thereof having an X-ray powder diffraction containing the following 2θ values measured using $CuK_\alpha$ radiation: 4.9, 8.0, 9.7 and at least one value selected from the group consisting of 5.4, 5.9, 10.4, 12.4, 17.7, 19.6 and 23.7.*

*51. Crystalline Form IV atorvastatin or a hydrate thereof having an X-ray powder diffraction containing the following 2θ values measured using $CuK_\alpha$ radiation: 8.0, 9.7, 19.6 and at least one value selected from the group consisting of 4.9, 12.4 and 21.7.*

*52. A crystalline Form I atorvastatin hydrate having an X-ray powder diffraction containing the following 2θ values measured using $CuK_\alpha$ radiation: 9.2, 9.5, 10.3, 10.6 and 22.0.*

*53. A crystalline Form I atorvastatin hydrate having an X-ray powder diffraction containing the following 2θ values measured using $CuK_\alpha$ radiation: 9.2, 9.5, 10.3, 10.6 and 11.9.*

*54. A crystalline Form I atorvastatin hydrate having an X-ray powder diffraction containing the following 2θ values measured using $CuK_\alpha$ radiation: 9.2, 9.5, 10.3, 10.6, 11.9, 21.6 and 22.0.*

55. A crystalline Form I atorvastatin hydrate having an X-ray powder diffraction containing the following 2θ values measured using CuK$_\alpha$ radiation: 9.2, 9.5, 10.3, 10.6, 17.1, 19.5 and 21.6.

56. Crystalline Form II atorvastatin or a hydrate thereof having an X-ray powder diffraction containing the following 2θ values measured using CuK$_\alpha$ radiation: 5.6, 8.5, 9.0, 12.4 (broad), 17.1–17.4 (broad) and 20.5.

57. Crystalline Form II atorvastatin or a hydrate thereof having an X-ray powder diffraction containing the following 2θ values measured using CuK$_\alpha$ radiation: 5.6, 8.5, 9.0, 12.4 (broad) and 17.1–17.4 (broad).

58. Crystalline Form IV atorvastatin or a hydrate thereof having an X-ray powder diffraction containing the following 2θ values measured using CuK$_\alpha$ radiation: 4.9, 8.0, 9.7 and 12.4.

59. Crystalline Form IV atorvastatin or a hydrate thereof having an X-ray powder diffraction containing the following 2θ values measured using CuK$_\alpha$ radiation: 4.9, 8.0, 9.7, 12.4 and at least one value selected from the group consisting of 5.4, 5.9, 10.4, 17.7, 18.4, 19.2, 19.6, 21.7, 23.0, 23.7 and 24.1.

60. Crystalline Form IV atorvastatin or a hydrate thereof having an X-ray powder diffraction containing the following 2θ values measured using CuK$_\alpha$ radiation: 4.9, 8.0, 9.7, 12.4 and 19.6.

61. A crystalline Form I atorvastatin hydrate having an X-ray powder diffraction containing the following 2θ value measured using CuK$_\alpha$ radiation: 11.9; and further characterized by solid state $^{13}$C nuclear magnetic resonance having the following chemical shift differences between the lowest ppm resonance and other resonances: 3.9, 5.1, 43.6, 46.8, 49.2 and 51.8.

62. A crystalline Form I atorvastatin hydrate having an X-ray powder diffraction containing the following 2θ value measured using CuK$_\alpha$ radiation: 22.0; and further characterized by solid state $^{13}$C nuclear magnetic resonance having a chemical shift difference between the lowest ppm resonance and another resonance of 5.1.

63. A crystalline Form I atorvastatin hydrate having an X-ray powder diffraction containing the following 2θ value measured using CuK$_\alpha$ radiation: 22.0; and further characterized by solid state $^{13}$C nuclear magnetic resonance having a chemical shift difference between the lowest ppm resonance and another resonance of 51.8.

64. A crystalline Form I atorvastatin hydrate having an X-ray powder diffraction containing the following 2θ value measured using CuK$_\alpha$ radiation: 22.0; and further characterized by solid state $^{13}$C nuclear magnetic resonance having the following chemical shift differences between the lowest ppm resonance and other resonances: 3.9, 5.1, 43.6, 46.8, 49.2 and 51.8.

65. A crystalline Form I atorvastatin hydrate having an X-ray powder diffraction containing the following 2θ values measured using CuK$_\alpha$ radiation: 9.2 and 11.9; and further characterized by solid state $^{13}$C nuclear magnetic resonance having the following chemical shift expressed in parts per million: 182.8.

66. A crystalline Form I atorvastatin hydrate having an X-ray powder diffraction containing the following 2θ values measured using CuK$_\alpha$ radiation: 9.2 and 22.0; and further characterized by solid state $^{13}$C nuclear magnetic resonance having the following chemical shift expressed in parts per million: 182.8.

67. A crystalline Form I atorvastatin hydrate having an X-ray powder diffraction containing the following 2θ value measured using CuK$_\alpha$ radiation: 11.9; and further characterized by solid state $^{13}$C nuclear magnetic resonance having the following chemical shifts expressed in parts per million: 21.3, 25.2, 26.4, 40.2, 41.9, 47.4, 64.9, 68.1, 70.5, 73.1, 113.8, 118.2, 120.9, 123.5, 127.6, 129.5, 131.1, 134.9, 137.0, 159.3, 166.7 (broad), 178.4 and 182.8.

68. A crystalline Form I atorvastatin hydrate having an X-ray powder diffraction containing the following 2θ value measured using CuK$_\alpha$ radiation: 22.0; and further characterized by solid state $^{13}$C nuclear magnetic resonance having the following chemical shifts expressed in parts per million: 21.3, 25.2, 26.4, 40.2, 41.9, 47.4, 64.9, 68.1, 70.5, 73.1, 113.8, 118.2, 120.9, 123.5, 127.6, 129.5, 131.1, 134.9, 137.0, 159.3, 166.7 (broad), 178.4 and 182.8.

69. A crystalline Form I atorvastatin hydrate having an X-ray powder diffraction containing the following 2θ values measured using CuK$_\alpha$ radiation: 11.9 and 22.0; and further characterized by solid state $^{13}$C nuclear magnetic resonance having the following chemical shifts expressed in parts per million: 21.3, 25.2, 26.4, 40.2, 41.9, 47.4, 64.9, 68.1, 70.5, 73.1, 113.8, 118.2, 120.9, 123.5, 127.6, 129.5, 131.1, 134.9, 137.0, 159.3, 166.7 (broad), 178.4 and 182.8.

70. The crystalline Form I atorvastatin hydrate of claim 45 containing about 1 to 8 moles of water.

71. The crystalline Form I atorvastatin hydrate of claim 47 containing about 1 to 8 moles of water.

72. The crystalline Form I atorvastatin hydrate of claim 52 containing about 1 to 8 moles of water.

73. The crystalline Form I atorvastatin hydrate of claim 53 containing about 1 to 8 moles of water.

74. The crystalline Form I atorvastatin hydrate of claim 54 containing about 1 to 8 moles of water.

75. The crystalline Form I atorvastatin hydrate of claim 55 containing about 1 to 8 moles of water.

76. The crystalline Form I atorvastatin hydrate of claim 61 containing about 1 to 8 moles of water.

77. The crystalline Form I atorvastatin hydrate of claim 62 containing about 1 to 8 moles of water.

78. The crystalline Form I atorvastatin hydrate of claim 63 containing about 1 to 8 moles of water.

79. The crystalline Form I atorvastatin hydrate of claim 64 containing about 1 to 8 moles of water.

80. The crystalline Form I atorvastatin hydrate of claim 65 containing about 1 to 8 moles of water.

81. The crystalline Form I atorvastatin hydrate of claim 66 containing about 1 to 8 moles of water.

82. The crystalline Form I atorvastatin hydrate of claim 67 containing about 1 to 8 moles of water.

83. The crystalline Form I atorvastatin hydrate of claim 68 containing about 1 to 8 moles of water.

84. The crystalline Form I atorvastatin hydrate of claim 69 containing about 1 to 8 moles of water.

85. The crystalline Form I atorvastatin hydrate of claim 45 containing 3 moles of water.

86. The crystalline Form I atorvastatin hydrate of claim 47 containing 3 moles of water.

87. The crystalline Form I atorvastatin hydrate of claim 52 containing 3 moles of water.

88. The crystalline Form I atorvastatin hydrate of claim 53 containing 3 moles of water.

89. The crystalline Form I atorvastatin hydrate of claim 54 containing 3 moles of water.

90. The crystalline Form I atorvastatin hydrate of claim 55 containing 3 moles of water.

91. The crystalline Form I atorvastatin hydrate of claim 61 containing 3 moles of water.

92. The crystalline Form I atorvastatin hydrate of claim 62 containing 3 moles of water.

93. The crystalline Form I atorvastatin hydrate of claim 63 containing 3 moles of water.

94. The crystalline Form I atorvastatin hydrate of claim 64 containing 3 moles of water.

95. The crystalline Form I atorvastatin hydrate of claim 65 containing 3 moles of water.

96. The crystalline Form I atorvastatin hydrate of claim 66 containing 3 moles of water.

97. The crystalline Form I atorvastatin hydrate of claim 67 containing 3 moles of water.

98. The crystalline Form I atorvastatin hydrate of claim 68 containing 3 moles of water.

99. The crystalline Form I atorvastatin hydrate of claim 69 containing 3 moles of water.

100. Crystalline Form II atorvastatin or a hydrate thereof having an X-ray powder diffraction containing the following $2\theta$ values measured using $CuK_\alpha$ radiation: 9.0, 20.5 and at least one value selected from the group consisting of 5.6, 7.4, 8.5, 15.8 (broad) and 25.7 (broad); and further characterized by solid state $^{13}C$ nuclear magnetic resonance having the following chemical shift difference between the lowest ppm resonance and another resonance of 4.7.

101. Crystalline Form II atorvastatin or a hydrate thereof having an X-ray powder diffraction containing the following $2\theta$ values measured using $CuK_\alpha$ radiation: 9.0, 20.5 and at least one value selected from the group consisting of 5.6, 7.4, 8.5, 15.8 (broad) and 25.7 (broad); and further characterized by solid state $^{13}C$ nuclear magnetic resonance having the following chemical shift difference between the lowest ppm resonance and another resonance of 47.8.

102. Crystalline Form II atorvastatin or a hydrate thereof having an X-ray powder diffraction containing the following $2\theta$ values measured using $CuK_\alpha$ radiation: 9.0, 20.5 and at least one value selected from the group consisting of 5.6, 7.4, 8.5, 15.8 (broad) and 25.7 (broad); and further characterized by solid state $^{13}C$ nuclear magnetic resonance having the following chemical shift differences between the lowest ppm resonance and other resonances: 4.7, 44.5, 45.2, 46.2 and 47.8.

103. Crystalline Form II atorvastatin or a hydrate thereof having an X-ray powder diffraction containing the following $2\theta$ values measured using $CuK_\alpha$ radiation: 9.0, 20.5 and at least one value selected from the group consisting of 5.6, 7.4, 8.5, 15.8 (broad) and 25.7 (broad); and further characterized by solid state $^{13}C$ nuclear magnetic resonance having the following chemical shifts expressed in parts per million: 22.8 (broad), 27.5, 40.2, 41.7, 42.3, 43.4, 67.3, 68.0, 69.0, 70.6, 114.7, 115.7, 117.1, 119.0, 120.3, 121.4, 122.9, 129.0, 133.3, 134.8, 140.5, 161 (broad), 163 (broad) and 181 (broad).

104. Crystalline Form II atorvastatin or a hydrate thereof having an X-ray powder diffraction containing the following $2\theta$ values measured using $CuK_\alpha$ radiation: 8.5 and 9.0; and further characterized by solid state $^{13}C$ nuclear magnetic resonance having the following chemical shifts expressed in parts per million: 140.5 and 181 (broad).

105. Crystalline Form II atorvastatin or a hydrate thereof having an X-ray powder diffraction containing the following $2\theta$ values measured using $CuK_\alpha$ radiation: 8.5, 9.0 and at least one value selected from the group consisting of 7.4, 12.4, (broad), 15.8 (broad), 17.1–17.4 (broad), 19.5, 20.5, 22.7–23.2 (broad) and 25.7 (broad); and further characterized by solid state $^{13}C$ nuclear magnetic resonance having the following chemical shifts expressed in parts per million: 140.5 and 181 (broad).

106. Crystalline Form IV atorvastatin or a hydrate thereof having an X-ray powder diffraction containing the following $2\theta$ value measured using $CuK_\alpha$ radiation: 8.0; and further characterized by solid state $^{13}C$ nuclear magnetic resonance having the following chemical shifts expressed in parts per million: 127.1, 184.9 and 186.4.

107. Crystalline Form IV atorvastatin or a hydrate thereof having an X-ray powder diffraction containing the following $2\theta$ values measured using $CuK_\alpha$ radiation: 8.0 and 9.7; and further characterized by solid state $^-C$ nuclear magnetic resonance having the following chemical shifts expressed in parts per million: 127.1, 184.9 and 186.4.

108. Crystalline Form IV atorvastatin or a hydrate thereof having an X-ray powder diffraction containing the following $2\theta$ values measured using $CuK_\alpha$ radiation: 4.9, 8.0 and 9.7; and further characterized by solid state $^{13}C$ nuclear magnetic resonance having the following chemical shifts expressed in parts per million: 127.1, 184.9 and 186.4.

109. Crystalline Form IV atorvastatin or a hydrate thereof having an X-ray powder diffraction containing the following $2\theta$ values measured using $CuK_\alpha$ radiation: 8.0, 9.7 and 19.6; and further characterized by solid state $^{13}$C nuclear magnetic resonance having the following chemical shifts expressed in parts per million: 127.1, 184.9 and 186.4.

110. A crystalline Form I atorvastatin hydrate having an X-ray powder diffraction containing the following 2θ values measured using CuK$_\alpha$ radiation: 9.2, 9.5, 10.3, 10.6, 11.9, 12.2, 17.1, 19.5, 21.6, 22.0, 22.7, 23.3, 23.7, 24.4, 28.9 and 29.2; and further characterized by solid-state $^{13}$C nuclear magnetic resonance having the following chemical shifts expressed in parts per million: 21.3, 25.2, 26.4, 40.2, 41.9, 47.4, 64.9, 68.1, 70.5, 73.1, 113.8, 118.2, 120.9, 123.5, 127.6, 129.5, 131.1, 134.9, 137.0, 159.3, 166.7 (broad), 178.4 and 182.8.

111. The crystalline Form I atorvastatin hydrate of claim 110 containing about 1 to 8 moles of water.

112. The crystalline Form I atorvastatin hydrate of claim 110 containing 3 moles of water.

113. Crystalline Form II atorvastatin or a hydrate thereof having an X-ray powder diffraction containing the following 2θ values measured using CuK$_\alpha$ radiation: 5.6, 7.4, 8.5, 9.0, 12.4 (broad), 15.8 (broad), 17.1–17.4 (broad), 19.5, 20.5, 22.7–23.2 (broad), 25.7 (broad) and 29.5; and further characterized by solid state $^{13}$C nuclear magnetic resonance having the following chemical shifts expressed in parts per million: 22.8 (broad), 27.5, 40.2, 41.7, 42.3, 43.4, 67.3, 68.0, 69.0, 70.6, 114.7, 115.7, 117.1, 119.0, 120.3, 121.4, 122.9, 129.0, 133.3, 134.8, 140.5, 161 (broad), 163 (broad) and 181 (broad).

114. Crystalline Form IV atorvastatin or a hydrate thereof having an X-ray powder diffraction containing the following 2θ values measured using CuK$_\alpha$ radiation: 4.9, 5.4, 5.9, 8.0, 9.7, 10.4, 12.4, 17.7, 18.4, 19.2, 19.6, 21.7, 23.0, 23.7 and 24.1; and further characterized by solid state $^{13}$C nuclear magnetic resonance having the following chemical shifts expressed in parts per million: 17.9, 19.4, 20.3, 25.9, 40.0, 42.1, 43.4, 46.1, 63.5, 66.3, 67.9, 71.5, 115.7, 119.8, 122.7, 127.1, 129.2, 134.7, 138.1 (broad), 159.0 (broad), 166.1 (broad), 179.3, 181.4, 184.9 and 186.4.

115. A crystalline Form I atorvastatin hydrate having an X-ray powder diffraction containing the following 2θ values measured using CuK$_\alpha$ radiation: 9.2, 9.5, 10.3, 10.6, 11.9 and 12.2.

116. Crystalline Form II atorvastatin or a hydrate thereof having an X-ray powder diffraction containing the following 2θ values measured using CuK$_\alpha$ radiation: 5.6, 8.5, 9.0, 12.4 (broad), 15.8 (broad) and 17.1–17.4 (broad).

117. Crystalline Form IV atorvastatin or a hydrate thereof having an X-ray powder diffraction containing the following 2θ values measured using CuK$_\alpha$ radiation: 4.9, 5.4, 8.0 and 12.4.

\* \* \* \* \*